United States Patent [19]

Jardieu et al.

[11] Patent Number: 5,622,700
[45] Date of Patent: Apr. 22, 1997

[54] METHOD FOR TREATING A LFA-1-MEDIATED DISORDER

[75] Inventors: Paula M. Jardieu, Berkeley; Bruce Montgomery, Redwood City, both of Calif.

[73] Assignee: Genentech, Inc., South San Francisco, Calif.

[21] Appl. No.: 432,543

[22] Filed: May 2, 1995

Related U.S. Application Data

[63] Continuation of Ser. No. 287,055, Aug. 8, 1994, which is a continuation of Ser. No. 128,329, Sep. 28, 1993, abandoned, which is a continuation of Ser. No. 933,269, Aug. 21, 1992, abandoned.

[51] Int. Cl.$^6$ .............................................. A61K 39/395
[52] U.S. Cl. ................................ 424/144.1; 424/130.1; 424/133.1; 424/141.1; 424/143.1; 424/152.1; 424/153.1; 424/154.1; 424/172.1; 424/173.1
[58] Field of Search .......................... 424/130.1, 133.1, 424/141.1, 143.1, 144.1, 152.1, 153.1, 159.1; 530/387.1, 388.1, 388.7, 388.73, 388.75; 514/9, 11

[56] References Cited

U.S. PATENT DOCUMENTS

| | | |
|---|---|---|
| 4,797,277 | 1/1989 | Arfors . |
| 5,002,869 | 3/1991 | Scholssman et al. . |
| 5,071,964 | 12/1991 | Dustin et al. . |
| 5,235,049 | 8/1993 | McClelland . |
| 5,284,931 | 2/1994 | Springer et al. . |
| 5,292,636 | 3/1994 | Kung et al. . |
| 5,475,091 | 12/1995 | Springer et al. ............... 530/388.22 |

FOREIGN PATENT DOCUMENTS

| | | | |
|---|---|---|---|
| 15518/88 | 10/1988 | Australia | C07K 13/00 |
| 15509/88 | 7/1989 | Australia . | |
| 2008368 | 1/1990 | Canada | C12P 21/08 |
| 0289949 | 11/1988 | European Pat. Off. | C12N 15/00 |
| 0346078 | 12/1989 | European Pat. Off. | A61K 39/395 |
| 0379904 | 8/1990 | European Pat. Off. | C07K 13/00 |
| 0387668 | 9/1990 | European Pat. Off. | C12N 15/12 |
| WO88/06592 | 9/1988 | WIPO | C07H 21/04 |
| WO90/08187 | 7/1990 | WIPO | C12N 15/00 |
| WO90/10652 | 9/1990 | WIPO | C07K 15/14 |
| WO90/15152 | 12/1990 | WIPO . | |
| WO90/15076 | 12/1990 | WIPO | C07K 15/28 |
| WO91/16927 | 11/1991 | WIPO . | |
| WO91/18011 | 11/1991 | WIPO | C07K 5/08 |
| WO91/16928 | 11/1991 | WIPO | A61K 39/395 |
| WO92/22653 | 12/1992 | WIPO | C12N 15/13 |
| WO93/06864 | 4/1993 | WIPO | A61K 39/395 |
| WO94/02175 | 2/1994 | WIPO | A61K 39/395 |

OTHER PUBLICATIONS

Masroor et al. Transplant. Immunol. 2: 176–189 (1994).
Ward et al. Therapeutic Immunol. 1: 165–171 (1994).
Harris Tibtech 11: 42–44 (1993).
Winter et al. Tips 14: 139–143 (1993).
Edgington Biotechnology 10: 383–389 (1992).
Wee et al. Transplantation 58: 261–264 (1994).
Tufveson Immunol. Reviews 136: 99–109 (1993).
McCabe Cell Immunol. 150:364–375 (1993).
Waldmann Ann Rev Immunol. 7: 407–444 (1989).
Stoppa et al Transplant Int. 4: 3–7 (1991).
Hutchings et al. Nature 348: 639–642 (1990).
Tilney et al. Transplantation 52: 389–398 (1991).
Benjamin et al Eur J. Immunol. 18:1079–1088 (1988).
Shizuru et al Science 240: 659–662 (1993).
Campbell et al. PNAS 86: 4282–4286 (1989).
Armitage et al., "The Clinical Trial of FK 506 as Primary and Rescue Immunosuppression in Pediatric Cardiac Transplantation" *Transplantation Proceedings* 23 (6):3058–3060 (Dec. 1991).
Babany et al., "Evaluation of the in vivo Dose–Response Relationship of Immunosupressive Drugs Using a Mouse Heart Transplant Model: Application of Cyclosporine" *The Journal of Pharmacology and Experimental Therapeutics* 244 (1):259–262 (1988).
Barker et al., "Keratinocytes as Initiators of Inflammation" *Lancet* 337:211–214 (Jan. 26, 1991).
Baume et al., "Failure of a CD18/Anti–LFA1 Monclonal Antibody Infusion to Prevent Graft Rejection in Leukemic Patients Receiving T-Depleted Allogeneic Bone Marrow Transplantation" *Transplantation* 47 (3): 472–474 (Mar. 1989).
Benjamin et al., "Mechanisms of Monoclonal Antibody–Facilitated Tolerance Induction: A Possible Role for the DC4 (L3T4) and CD11a (LFA–1) Molecules in Self–Non–self Discrimination" *European Journal of Immunology* 18:1079–1088 (1988).
Berlin et al., "Monoclonal Antibodies Against Human T Cell Adhesion Molecules–Modulation of Immune Function in Nonhuman Primates" *Transplantation* 53(4):840–849 (1992).
Blakeslee, "New Technique in Lab Prevents Rejection of Organ Transplants" *The New York Times* p. B6 (Mar. 10, 1992).
Busing et al., "Is Long–Term Therapy Without Cyclosporin A (CsA) Indispensable or Dangerous? One–Year Results of a Prospective Randomized Trial" *Transplantation Proceedings* 21(1):1601–1603 (Feb. 1989).
Campbell, "Intercellular Adhesion Molecule 1 is Induced on Isolated Endocrine Islet Cells by Cytokines but not by Reovirus Infection" *Proc. Natl. Acad. Sci. USA* 86:4282–4286 (1989).

(List continued on next page.)

*Primary Examiner*—Christina Y. Chan
*Assistant Examiner*—Phillip Gambel
*Attorney, Agent, or Firm*—Wendy M. Lee

[57] ABSTRACT

A method is provided for administering to a mammal suffering from, or at risk for, a LFA-1-mediated disorder an initial dosing of a therapeutically effective amount of LFA-1 antagonist, followed by a subsequent intermittent dosing of a therapeutically effective amount of LFA-1 antagonist that is less than 100%, calculated on a daily basis, of the initial dosing of antagonist.

37 Claims, 10 Drawing Sheets

OTHER PUBLICATIONS

Carpenter et al., "Prophylactic Use of Monoclonal Anti–IL–2 Receptor Antibody in Cadaveric Renal Transplantation" *American Journal of Kidney Diseases* XIV(5):54–57 (Nov. 1989).

Cobbold et al., "Therapy With Monoclonal Antibodies by Elimination of T–cell subsets in vivo" *Nature* 312 (6):548–551 (Dec. 1984).

Cosimi et al., "Immunosuppression of Cynomolgus Receipients of Renal Allografts to R6.5, a Monoclonal Antibody to Intercellular Adhesion Molecule-1" *In Leukocyte Adhesion Molecules*, Springer–Verlag pp. 274–281 (1988).

Cosimi et al., "In Vivo Effects of Monoclonal Antibody to ICAM–1 (CD54) in Nonhuman Primates with Renal Allografts" *The Journal of Immunology* 144 (12):4604–4612 (Jun. 15, 1990).

Cunningham, "Anomolous Features of Allogeneic Reactions" *Understanding Immunology* (Chapter 10), New York: Academic Press pp. 158–159 (1978).

Cyclosporine Label, "Product Information" *Physicians Desk Reference* 49 (1995).

Dantal et al., "Use of Monoclonal Antibodies in Human Transplantation" *Current Opinion in Immunology* 3:740–747 (1991).

Davignon et al., "Monoclonal Antibody to a Novel Lymphocyte Function–Associated Antigen (LFA–1): Mechanism of Blockade of T Lymphocyte–Mediated Killing and Effects on Other T and B Lymphocyte Functions" *The Journal of Immunology* 127(2):590–595 (Aug. 1981).

Dustin et al., "Induction By IL 1 and Interferon–γ: Tissue Distribution, Biochemistry, and Function of a Natural Adherence Molecule (ICAM–1)[1]" *The Journal of Immunology* 137 (1):245–254 (Jul. 1, 1986).

Edgington, "How Sweet It Is: Selection–Mediating Drugs" *Bio/Technology* 10:383–389 (Apr. 1992).

Fekete et al., "Involvement of Lyphocyte Function–Associated Antigen-1 (LFA–1_But Not ICAM–1 in a Radioactive Leukocyte Cell–Mediated Immunity LA–CMI) Assay" *J. Clin. Lab. Immunol.* 31:145–149 (1990).

First et al. *Clin. Transplant* 2:185–189 (1988).

Fischer, "Anti–LFA–1 Antibody as Immunosuppressive Reagent in Transplantation" *Chem. Immunol.* 50:89–97 (1991).

Fischer et al., "Prevention of Graft Failure by an Anti–HLFA–1 Monoclonal Antibody in HLA–Mismatched Bone–Marrow Transplantation" *Lancet* pp. 1058–1061 (Nov. 8, 1986).

Fischer et al., "Reduction of Graft Failure by a Monoclonal Antibody (Anti–LFA–1 CD11a) After HLA Nonidentical Bone Marrow Transplantation in Children with Immunodeficiencies" *Blood* 77 (2):249–256 (Jan. 15, 1991).

Fischer et al., "Role of the LFA–1 Molecule in Cellular Interactions Required For Antibody Production in Humans[1]" *The Journal of Immunology* 136 (9):3198–3203 (May 1, 1986).

Goebeler et al., "Expression of Intercellular Adhesion Molecule–1 in Murine Allergic Contact Dermatitis" *Int. Arch. Allergy Appl. Immunol.* 93:294–299 (1990).

Harris et al., "Therapeutic Antibodies—The Coming of Age" *TIBTECH* 11:42–44 (Feb. 1993).

Heagy et al., "Potent Ability of Anti–LFA–1 Monoclonal Antibody to Prolong Allograft Survival" *Transplantation* 37:520–523 (1984).

Herbert et al., "Strategies of Monoclonal Antibody Therapy That Induce Permanent Tolerance of Organ Transplants" *Transplantation* 46:128S–134S (Aug. 1988).

Hildreth et al., "A Human Lymphocyte–associated Antigen Involved in Cell–mediated Lympholysis" *European Journal of Immunology* 13:202–208 (1983).

Hourmant et al., "Administration of an Anti–CD11a Monoclonal Antibody in Recipients of Kidney Transplantation" *Transplantation* 58 (3):377–380 (Aug. 1994).

Hutchings et al., "Transfer of Diabetes in Mice Prevented by Blockade of Adhesion–Promoting Receptor on Macrophages" *Nature* 348:639–642 (Dec. 13, 1990).

Isaacs et al., "Humanised Monoclonal Antibody Therapy for Rheumatoid Arthritis" *Lancet* 340:748–752 (Sep. 26, 1992).

Isobe et al., "Specific Acceptance of Cardiac Allograft After Treatment with Antibodies to ICAM–I and LFA–1" *Science* pp. 1125–1127 (Feb. 1992).

Jendrisak et al., "Prolongation in Murine Cardiac Allograft Survival With Monoclonal Antibodies to LFA–1, ICAM–1, and CD4" *Transplantation Proceedings* 25 (1):825–827 (Feb. 1993).

Jensen et al., "Pediatric Renal Transplantation Under FK 506 Immunosuppression" *Transplantation Proceedings* 23 (6):3075–3077 (Dec. 1991).

Kahana et al., "OKT3 Prophylaxis Versus Conventional Drug Therapy: Single–Center Perspective, Part of a Multicenter Trial" *American Journal of Kidney Diseases* XIV (5):5–9 (Nov. 1989).

Komori et al., "Role of ICAM–1 and LFA–1 in Cardiac Allograft Rejection of the Rat" *Transplantation Proceedings* 25 (1):831–832 (Feb. 1993).

Krensky et al., "The Functional Significance, Distibution, and Structure of LFA–2, and LFA–3: Cell Surface Antigens Associated with CTL–Target Interactions[1]" *The Journal of Immunology* 131 (2):611–616 (Aug. 1983).

Kuypers et al., "Leukocyte Membrane Adhesion Proteins LFA–1, CR3 and p150,95: A Review of Functional and Regulatory Aspects" *Res. Immunol.* 140:461–486 (1989).

Lakey et al., "Prevention of Recurrence of Insulin–Dependent Diabetes Mellitus in Islet Cell–Transplanted Diabetic NOD Mice Using Adjuvant Therapy" *Transplantation Proceedings* 24 (6):2848 (Dec. 1992).

Larson et al., "Structure and Function of Leukocyte Integrins" *Immunological Reviews* 114:181–217 (1990).

LeMauff et al., "Effect of Anti–LFA1 (CD11a) Monoclonal Antibodies in Acute Rejection in Human Kidney Transplantation" *Transplantation* 52 (2):291–296 (Aug. 1991).

Levinsky, "Recent Developments in Bone Marrow Transplantation" *Clinical Immunol. and Immunopathol.* 50 (1):S124–S132 (1989).

Lo et al., "Two Leukocyte Receptors (CD11a/CD18 and CD11b/CD18) Mediate Transient Adhesion to Endothelium by Binding to Different Ligands" *The Journal of Immunology* 143 (10):3325–3329 (Nov. 15, 1989).

Maraninchi et al., "Anti LFA–1 Monoclonal Antibody for the Prevention of Graft Rejection After T Cell–depleted HLA–matched Bone Marrow Transplantation for Leukemia in Adults" *Bone Marrow Transplantation* 4:147–150 (1989).

Masroor et al., "Monoclonal Antibodies in Organ Transplantation: An Overview" *Transplant Immunology* 2:176–189 (1994).

McCabe et al., "s'CAM–1 Enhances Cytokine Production Stimulated by Alloantigen" *Cellular Immunology* 150:364–375 (1993).

Mentzer et al., "LFA-1 Membrane Molecule in the Regulation of Homotypic Adhesions of Human B Lymphocytes" *The Journal of Immunology* 135 (1):9–11 (Jul. 1985).

Monaco, "Biological Immunosuppression: Polyclonal Antilymphocyte Sera, Monoclonal Antibody, and Donor-Specific Antigen Biological Immunosuppression: Polyclonal Antilymphocyte Sera, Monoclonal Antibody, and Donor-Specific Antigen" *Organ Transplantation and Replacement* (Chapter 5), G. James.

Morris et al., "A Study of the Contrasting Effects of Cyclosporine, FK 506, and Rapamycin on the Suppression of Allograft Rejection" *Transplantation Proceeding* 22 (4):1638–1641 (Aug. 1990).

Nakakura et al., "An Anti-Adhesion Molecule (LFA-1, CD11a) Monoclonal Antibody Suppresses Ongoing Rejection and Prolongs Heart Allograft Survival Indefinitely Without Lymphocyte Depletion" *The Journal of Heart and Lung Transplantation* 11 (1):130 (Jan./F 1992).

Nakakura et al., "Potent and Effective Prolongation by Anti-LFA-1 Monoclonal Antibody Monotherapy of Non-Primarily Vascularized Heart Allograft Survival in Mice Without T. Cell Depletion" *Transplantation* 55 (2):412–417 (Feb. 1993).

Nickoloff, "Keratinocyte Intercellular Adhesion Molecule-1(ICAM-1) Expression Precedes Dermal T Lymphocytic Infiltration in Allergic Contact" *Am. J. Pathol* 135:1045–1053 (1989).

Nickoloff, "Role of Interferon-γ in Cutaneous Trafficking of Lymphocytes with Emphasis on Molecular and Cellular Adhesion Events" *Arch Dermatol.* 124:1835–1843 (1988).

Nickoloff et al., "Cellular Localization of Interleukin-8 and its Inducer, Tumor Necrosis Factor-alpha in Psoriasis" *American Journal of Pathology* 138 (1):129–140 (Jan. 1991).

O'Reilly et al., "Characterization of Pancreatic Islet Cell Infiltrates in NOD Mice: Effect of Cell Transfer and Transgene Expression" *European Journal of Immunology* 21:1171–1179 (1991).

Perez et al., "In Vivo Infusion of Anti LFA-1 Antibody in HLA Non-identical Bone Marrow Transplantation in Children: Serum Concentrations and Biological Effects" *Bone Marrow Transplantation* 4:379–384 (1989).

Qin et al., "Complete Freund's Adjuvant-Induced T Cells Prevent the Development and Adoptive Transfer of Diabetes in Nonobese Diabetic Mice" *The Journal of Immunology* 150 (5):2072–2080 (Mar. 1, 1993).

Sanders et al., "Characterization of the Physical Interaction Between Antigen-Specific B and T Cells" *The Journal of Immunology* 137 (8):2395–2404 (Oct. 15, 1986).

Schorlemmer et al., "Therapeutic Effects of 15-Deoxyspegualin in Acute and Chronic Relapsing Experimental Allergic Encephalomyelitis (EAE) as Models for Multiple Sclerosis (MS)" *Drugs Exptl. Clin. Res.* XVII (10/11):461–469 (1991).

Schroeder et al., "Antimurine Antibody Formation Following OKT3 Therapy" *Transplantation* 49:48–51 (Jan. 1990).

Shapiro et al., "FK 506 in Clinical Kidney Transplantation" *Transplantation Proceedings* 23 (6):3065–3067 (Dec. 1991).

Shield et al., "The Reuse of OKT3 After Previous Rejection or Induction Therapy in Cadaveric Renal Transplantation" *American Journal of Kidney Disease* 14 (5 (Suppl. 2)):35–38 (1989).

Shizuru et al., "Immunotherapy of the Nonobese Diabetic Mouse: Treatment with an Antibody to T-Helper Lymphocytes" *Science* 240:659–662 (1988).

Stoppa et al., "Anti-LFA-1 Monoclonal Antibody (25.3) for Treatment of Steroid-resistant Grade III-IV Acute Graft-versus-host Disease" *Transplant International* 4:3–7 (1991).

Tilney et al., "Chronic Rejection-An Undefined Conundrum" *Transplantation* 52 (3):389–398 (09 1991).

Trager et al., "Cardiac Allograft Prolongation in Mice Treated with Combined Postransplantation Total-Lymphoid Irradiation and Anti-L3T4 Antibody Therapy" *Transplantation* 47 (4):587–591 (Apr. 1989).

Tufveson, "New Immunosuppressants: Testing and Development in Animal Models and the Clinic: with Special Reference to DSG" *Immunol. Reviews* 136:99–109 (1993).

Twaddell, "Clinical Experience with rhuMab HER2 in Metastatic Breast Cancer" *Antibody Engineering* (Abstract) Sixth IBC Internatio (1995).

Van Brunt, "Therapeutic Antibodies (Finally) Come of Age" *Bioworld Financial Watch* 3 (29):1–11 (Jul. 17, 1995).

Van Dijken, "Evidence That Anti-LFA-1 in vivo Improves Engraftment and Survival After Allogeneic Bone Marrow Transplantation" *Transplantation* 49 (5):882–886 (May 1990).

Waid et al., "T10B9.1A-31 Anti-T-Cell Monoclonal Antibody: Preclinical Studies and Clinical Treatment of Solid Organ Allograft Rejection" *American Journal of Kidney Diseases* XIV (5):61–70 (Nov. 1989).

Waldmann, "Immune Receptors: Targets for Therapy of Leukemia/Lymphoma, Autoimmune Diseases and for the Prevention of Allograft Rejection" *Annu. Rev. Immunol.* 10:675–704 (1992).

Waldmann, "Manipulation of T-Cell Responses with Monoclonal Antibodies" *Ann. Rev. Immunol.* 7:407–444 (1989).

Waldmann, T., "Monoclonal Antibodies in Diagnosis and Therapy" *Science* 252:1657–1662 (Jun. 1991).

Ward et al., "Blocking of Adhesion Molecules in vivo as Anti-Inflammatory Therapy" *Therapeutic Immunology* 1:165–171 (1994).

Warren et al., "Differential Survival of Heart and Skin Allografts in Inbred Rats" *Transplantation Proceedings* V (1):717–719 (Mar. 1973).

Wee et al., "Anti-CD4 mAb Therapy Significantly Delays the Alloantibody Response in a Cynomolgus Renal Transplant Model" *Transplantation* 58 (2):261–264 (Jul. 1994).

Whitham et al., "Location of a New Encephalitogenic Epitope (Residues 43 to 64) in Proteolopid Protein That Induces Relapsing Experimental Autoimmune Encephalomyelitis in PL/J and (SJL x PL) $F_1$ Mice" *The Journal of Immunology* 147 (11):3803–3808 (Dec. 1, 1991).

Winter, "Antibody-based Therapy—Humanized Antibodies" *TIPS*, UK: Elsevier Science Publishers vol. 14:139–143 (1993).

Yednock et al., "Prevention of Experimental Autoimmune Encephalomyelitis by Antibodies Against α4β1 Integrin" *Nature* 356:63–66 (Mar. 5, 1992).

McMurray et al. Seminars Arthr. Rheum. 25: 215–233 (1996).

Rizova. et al. J. Dermatol. Sci 7: 143 (1994).

FIG. 4
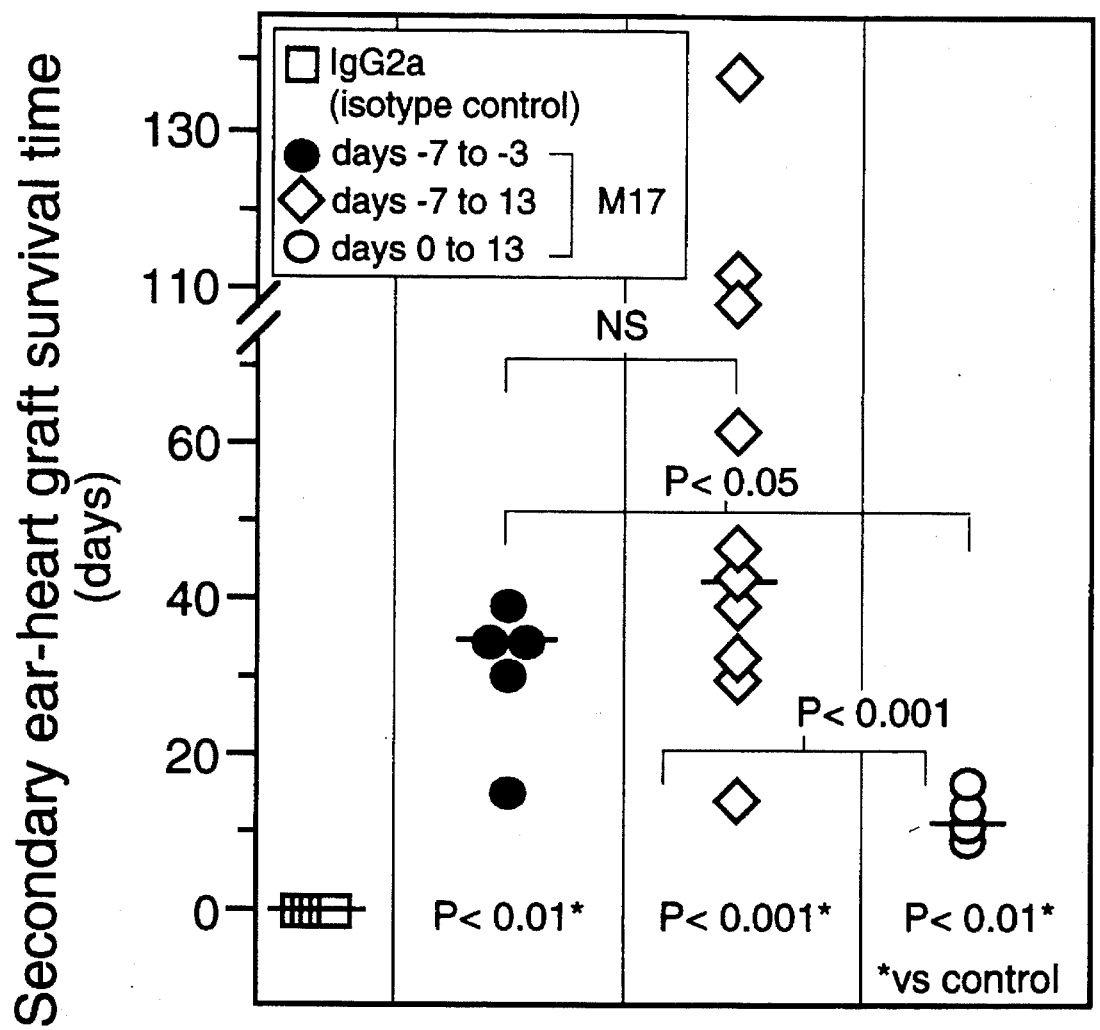
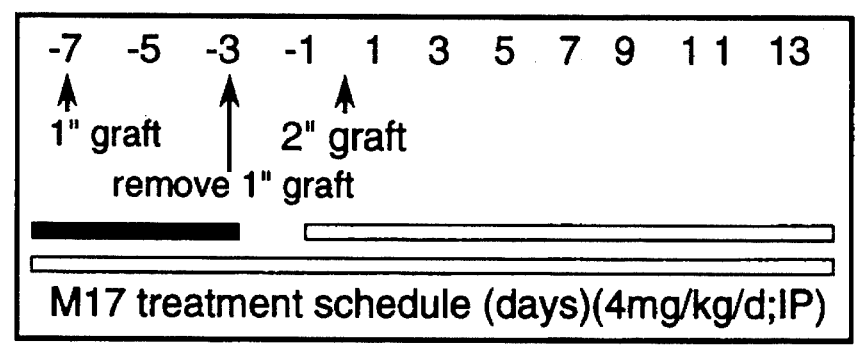

METHOD FOR TREATING A LFA-1-MEDIATED DISORDER

CROSS REFERENCE

This application is a continuation of co-pending U.S. application Ser. No. 08/287,055 filed 8 Aug. 1994, pending, which application is a continuation of U.S. application Ser. No. 08/128,329 filed 28 Sep. 1993 (abandoned), which application is a continuation of U.S. application Ser. No. 07/933,269 filed 21 Aug. 1992 (abandoned), which applications are incorporated herein by reference and to which applications priority is claimed under 35 USC §120.

BACKGROUND OF THE INVENTION

1. Field of the Invention

This invention relates to a method for treating mammals, preferably humans, who suffer from unwanted immune responses. In particular, it relates to methods for ameliorating LFA-1-mediated disorders, such as those caused by transplanted grafts and immune diseases.

2. Description of Background and Related Art

The treatment of disorders and diseases mediated by T lymphocytes has been addressed through many routes. Rheumatoid arthritis (RA) is one such disorder. Current therapy for RA includes bed rest, application of heat, and drugs. Salicylate is the currently preferred drug, particularly as other alternatives such as immunosuppressive agents and adrenocorticosteroids can cause greater morbidity than the underlying disease itself. Nonsteroidal anti-inflammatory drugs are available, and many of them have effective analgesic, anti-pyretic and anti-inflammatory activity in RA patients. These include indomethacin, phenylbutazone, phenylacetic acid derivatives such as ibuprofen and fenoprofen, naphthalene acetic acids (naproxen), pyrrolealkanoic acid (tometin), indoleacetic acids (sulindac), halogenated anthranilic acid (meclofenamate sodium), piroxicam, and diflunisal.

Other drugs for use in RA include anti-malarials such as chloroquine, gold salts and penicillamine. These alternatives frequently produce severe side effects, including retinal lesions and kidney and bone marrow toxicity. Immunosuppressive agents such as methotrexate have been used only in the treatment of severe and unremitting RA because of their toxicity. Corticosteroids also are responsible for undesirable side effects (e.g., cataracts, osteoporosis, and Cushing's disease syndrome) and are not well tolerated in many RA patients.

Another disorder mediated by T lymphocytes is rejection of host or grafts after transplantation. Attempts to prolong the survival of transplanted allografts and xenografts, or to prevent graft versus host rejection, both in experimental models and in medical practice, have centered mainly on the suppression of the immune apparatus of the recipient. This treatment has as its aim preventive immunosuppression and/or treatment of graft rejection.

Examples of agents used for preventive immunosuppression include cytotoxic drugs, anti-metabolites, corticosteroids, and anti-lymphocytic serum. Nonspecific immunosuppressive agents found particularly effective in preventive immunosuppression (azathioprine, bromocryptine, methylprednisolone, prednisone, and most recently, cyclosporin A) have significantly improved the clinical success of transplantation. The nephrotoxicity of cyclosporin A after renal transplantation has been reduced by co-administration of steroids such as prednisolone, or prednisolone in conjunction with azathioprine. In addition, kidneys have been grafted successfully using anti-lymphocyte globulin followed by cyclosporin A. Another protocol being evaluated is total lymphoid irradiation of the recipient prior to transplantation followed by minimal immunosuppression after transplantation.

Treatment of rejection has involved use of steroids, 2-amino-6-aryl-5-substituted pyrimidines, heterologous anti-lymphocyte globulin, and monoclonal antibodies to various leukocyte populations, including OKT-3. See generally *J. Pediatrics*, 111: 1004–1007 (1987), and specifically U.S. Pat. No. 4,665,077.

The principal complication of immunosuppressive drugs is infections. Additionally, systemic immunosuppression is accompanied by undesirable toxic effects (e.g., nephrotoxicity when cyclosporin A is used after renal transplantation) and reduction in the level of the hemopoietic stem cells. Immunosuppressive drugs may also lead to obesity, poor wound healing, steroid hyperglycemia, steroid psychosis, leukopenia, gastrointestinal bleeding, lymphoma, and hypertension.

In view of these complications, transplantation immunologists have sought methods for suppressing immune responsiveness in an antigen-specific manner (so that only the response to the donor alloantigen would be lost). In addition, physicians specializing in autoimmune disease strive for methods to suppress autoimmune responsiveness so that only the response to the self-antigen is lost. Such specific immunosuppression generally has been achieved by modifying either the antigenicity of the tissue to be grafted or the specific cells capable of mediating rejection. In certain instances, whether immunity or tolerance will be induced depends on the manner in which the antigen is presented to the immune system.

Pretreating the allograft tissues by growth in tissue culture before transplantation has been found in two murine model systems to lead to permanent acceptance across MHC barriers. Lafferty et al., *Transplantation*, 22: 138–149 (1976); Bowen et al., *Lancet*, 2:585–586 (1979). It has been hypothesized that such treatment results in the depletion of passenger lymphoid cells and thus the absence of a stimulator cell population necessary for tissue immunogenicity. Lafferty et al., *Annu. Rev. Immunol.*, 1: 143 (1983). See also Lafferty et al., *Science*, 188: 259–261 (1975) (thyroid held in organ culture), and Gores et al., *J. Immunol.*, 137: 1482–1485 (1986) and Faustman et al., *Proc. Natl. Acad. Sci. U.S.A.*, 78: 5156–5159 (1981) (islet cells treated with murine anti-Ia antisera and complement before transplantation). Also, thyroids taken from donor animals pretreated with lymphocytotoxic drugs and gamma radiation and cultured for ten days in vitro were not rejected by any normal allogeneic recipient. Gose and Bach, *J. Exp. Med.*, 249: 1254–1259 (1979). All of these techniques involve depletion or removal of donor lymphocyte cells.

In some models such as vascular and kidney grafts, there exists a correlation between Class II matching and prolonged allograft survival, a correlation not present in skin grafts. Pescovitz et al., *J. Exp. Med.*, 160: 1495–1508 (1984); Conti et al., *Transplant, Proc.*, 19: 652–654 (1987). Therefore, donor-recipient HLA matching has been utilized. Additionally, blood transfusions prior to transplantation have been found to be effective. Opelz et al., *Transplant. Proc.*, 4: 253 (1973); Persijn et al., *Transplant. Proc.*, 23: 396 (1979). The combination of blood transfusion before transplantation, donor-recipient HLA matching, and immunosuppression therapy (cyclosporin A) after transplantation was found to improve significantly the rate of graft survival, and the effects were found to be additive. Opelz et al., *Transplant. Proc.*, 17: 2179 (1985).

The transplantation response may also be modified by antibodies directed at immune receptors for MHC antigens. Bluestone et al., *Immunol. Rev.* 90: 5–27 (1986). Further, graft survival can be prolonged in the presence of antigraft antibodies, which lead to a host reaction that in turn produces specific immunosuppression. Lancaster et al., *Nature*, 315: 336–337 (1985).

The immune response of the host to MHC antigens may be modified specifically by using bone marrow transplantation as a preparative procedure for organ grafting. Thus, anti-T-cell monoclonal antibodies are used to deplete mature T cells from the donor marrow inoculum to allow bone marrow transplantation without incurring graft-versus-host disease. Mueller-Ruchholtz et al., *Transplant Proc.*, 8: 537–541 (1976). In addition, elements of the host's lymphoid cells that remain for bone marrow transplantation solve the problem of immunoincompetence occurring when fully allogeneic transplants are used.

Lymphocyte adherence to endothelium is a key event in the process of inflammation. There are at least three known pathways of lymphocyte adherence to endothelium, depending on the activation state of the T cell and the endothelial cell. T cell immune recognition requires the contribution of the T cell receptor as well as adhesion receptors, which promote attachment of T cells to antigen-presenting cells and transduce regulatory signals for T cell activation. The lymphocyte function associated (LFA) antigen-1 (LFA-1, CD11a, α-chain/CD18, β-chain) has been identified as the major integrin receptor on lymphocytes involved in these cell adherence interactions leading to several pathological states. ICAM-1, the endothelial cell immunoglobulin-like adhesion molecule, is a known ligand for LFA-1 and is implicated directly in graft rejection, psoriasis, and arthritis.

LFA-1 is required for a range of leukocyte functions, including lymphokine production of helper T cells in response to antigen-presenting cells, killer T cell-mediated target cell lysis, and immunoglobulin production through T cell-B cell interactions. Activation of antigen receptors on T cells and B cells allows LFA-1 to bind its ligand with higher affinity.

Monoclonal antibodies (MAbs) directed against LFA-1 led to the initial identification and investigation of the function of LFA-1. Davignon et al., *J. Immunol.*, 127: 590 (1981). LFA-1 is present only on leukocytes [Krenskey et al., *J. Immunol.*, 131: 611 (1983)], and ICAM-1 is distributed on activated leukocytes, dermal fibroblasts, and endothelium. Dustin et al., *J. Immunol.*, 137: 245 (1986).

Previous studies have investigated the effects of anti-CD11a MAbs on many T-cell-dependent immune functions in vitro and a limited number of immune responses in vivo. In vitro, anti-CD11a MAbs inhibit T-cell activation [Kuypers et al., *Res. Immunol.*, 140: 461 (1989)], T-cell-dependent B-cell proliferation and differentiation [Davignon et al., supra; Fischer et al., *J. Immunol.*, 136: 3198 (1986)], target cell lysis by cytotoxic T lymphocytes [Krensky et al., supra], formation of immune conjugates [Sanders et al., *J. Immunol.*, 137: 2395 (1986); Mentzer et al., *J. Immunol.*, 135: 9 (1985)], and the adhesion of T-cells to vascular endothelium. Lo et al., *J. Immunol.*, 143: 3325 (1989). Also, the antibody 5C6 directed against CD11b/CD18 was found to prevent intra-islet infiltration by both macrophages and T cells and to inhibit development of insulin-dependent diabetes mellitis in mice. Hutchings et al., *Nature*, 348: 639 (1990).

The observation that LFA-1-ICAM-1 interaction is necessary to optimize T cell function in vitro, and that anti-CD11a MAbs induce tolerance to protein antigens [Benjamin et al., *Eur. J. Immunol.*, 18: 1079 (1988)] and prolongs tumor graft survival in mice [Heagy et al., *Transplantation*, 37: 520–523 (1984)] was the basis for testing the MAbs to these molecules for prevention of graft rejection in humans.

Experiments have also been carried out in primates. For example, based on experiments in monkeys it has been suggested that a MAb directed against ICAM-1 can prevent or even reverse kidney graft rejection. Cosimi et al., "Immunosuppression of Cynomolgus Recipients of Renal Allografts by R6.5, a Monoclonal Antibody to Intercellular Adhesion Molecule-1," in Springer et al. (eds.), *Leukocyte Adhesion Molecules* (New York: Springer, 1988), p. 274; Cosimi et al., *J. Immunology*, 144: 4604–4612 (1990). Furthermore, the in vivo administration of anti-CD11a MAb to cynomolgus monkeys prolonged skin allograft survival. Berlin et al., *Transplantation*, 53: 840–849 (1992).

The first successful use of a rat anti-murine CD11a antibody (25-3; IgG1) in children with inherited disease to prevent the rejection of bone-marrow-mismatched haploidentical grafts was reported by Fischer et al., *Lancet*, 2: 1058 (1986). Minimal side effects were observed. See also Fischer et al., *Blood*, 77: 249 (1991); van Dijken et al., *Transplantation*, 49: 882 (1990); and Perez et al., *Bone Marrow Transplantation*, 4: 379 (1989). Furthermore, the antibody 25-3 was effective in controlling steroid-resistant acute graft-versus-host disease in humans. Stoppa et al., *Transplant. Int.*, 4: 3–7 (1991).

However, these results were not reproducible in leukemic adult grafting with this MAb [Maraninchi et al., *Bone Marrow Transplant*, 4: 147–150 (1989)], or with an anti-CD18 MAb, directed against the invariant chain of LFA-1, in another pilot study. Baume et al., *Transplantation*, 47: 472 (1989) Furthermore, a rat anti-murine CD11a MAb, 25-3, was unable to control the course of acute rejection in human kidney transplantation. LeMauff et al., *Transplantation*, 52: 291 (1991).

A review of the use of monoclonal antibodies in human transplantation is provided by Dantal and Soulillou, *Current Opinion in Immunology*, 3: 740–747 (1991).

A recent report showed that brief treatment with either anti-LFA-1 or anti-ICAM-1 MAbs minimally prolonged the survival of primarily vascularized heterotopic heart allografts in mice. Isobe et al., *Science*, 255: 1125 (1992). However, combined treatment with both MAbs was required to achieve long-term graft survival in this model.

Independently, it was shown that treatment with anti-LFA-1 MAb alone potently and effectively prolongs the survival of heterotopic (ear-pinnae) nonprimarily vascularized mouse heart grafts using a maximum dose of 4 mg/kg/day and treatment once a week after a daily dose. Nakakura et al., *J. Heart Lung Transplant.*, 11: 223 (1992). [See also *The New York Times*, p. B6 (Tuesday, Mar. 10, 1992) "New Technique in Lab Prevents Rejection of Organ Transplants," by Sandra Blakeslee.] Nonprimarily vascularized heart allografts are more immunogenic and more resistant to prolongation of survival by MAbs than primarily vascularized heart allografts. Warren et al., *Transplant, Proc.*, 5: 717 (1973) Trager et al., *Transplantation*, 47: 587 (1989). The latter reference discusses treatment with antibodies against L3T4 using a high initial dose and a lower subsequent dose.

Another study on treating a sclerosis-type disease in rodents using similar antibodies to those used by Nakakura et al., supra, is reported by Yednock et al., *Nature*, 356: 63–66 (1992).

Additional disclosures on the use of anti-LFA-1 antibodies and ICAM-1, ICAM-2, and LFA-3 and their antibodies to treat LFA-1-mediated disorders include WO 91/18011 published Nov. 28, 1991, WO 91/16928 published Nov. 14, 1991, WO 91/16927 published Nov. 14, 1991, Can. Pat. Appln. 2,008,368 published Jun. 13, 1991, WO 90/15076 published Dec. 13, 1990, WO 90/10652 published Sep. 20, 1990, EP 387,668 published Sep. 19, 1990, WO 90/08187 published Jul. 26, 1990, EP 379,904 published Aug. 1, 1990, EP 346,078 published Dec. 13, 1989, U.S. Pat. No. 5,071,964, U.S. Pat. No. 5,002,869, Australian Pat. Appln. 8815518 published Nov. 10, 1988, EP 289,949 published Nov. 9, 1988, and EP 303,692 published Feb. 22, 1989.

The above methods successfully utilizing anti-LFA-1 or anti-ICAM-1 antibodies represent an improvement over traditional immunosuppressive drug therapy however, they advocate a higher than minimum or fixed dosage of drug that we expect either to unduly suppress the immune system (and create a significant risk of infection) or to be inadequate for long-term tolerance. There is a need in the art to better treat disorders that are mediated by LFA-1 such as autoimmune diseases, graft vs. host or host vs. graft rejection, and T cell inflammatory responses, so as to minimize side effects and sustain specific tolerance to self- or xenoantigens.

Accordingly, it is an object of this invention to provide an improved method for sustaining resistance to LFA-1-mediated disorders with minimal side effects.

It is another object to prolong graft survival in transplants.

It is a further object to minimize the toxicity and other adverse effects arising from the use of large doses of immunosuppressants in transplant patients.

It is a still further object to provide the host with selective tolerance to the antigen or agent causing the specific immune disorder, so that the host has a reduced susceptibility to infections and other assaults on the immune system that are opportunistic when conventional immunosuppressive agents or dosages are employed.

These and other objects will become apparent to one of ordinary skill in the art.

SUMMARY OF THE INVENTION

These objects are accomplished by a method for treating a LFA-1-mediated disorder in a mammal comprising administering to the mammal an initial dosing of a therapeutically effective amount of an LFA-1 antagonist, followed by a subsequent intermittent dosing of a therapeutically effective amount of an LFA-1 antagonist that is less than 100%, calculated on a daily basis, of the initial dosing of LFA-1 antagonist, whereby the mammal has selective tolerance of the disorder. Preferably, the LFA-1 antagonist is an anti-LFA-1 antibody, in particular anti-CD11a.

It was surprisingly found that specific tolerance is induced by adjusting the dose regimen, and that it is not necessary to maintain antagonist dosage at the same initial level over the course of treatment. It was also surprising that the survival of grafts upon transplantation was prolonged using a dosing regimen where a high initial dose is given followed by a continuous maintenance dose. Also unexpected was that this dosing scheme using only one drug resulted in a selective tolerance of the host to the agent causing the disorder, so that the host defense system was not severely depressed.

The transplantation method herein is applicable to both allografts and xenografts, and the use of xenografts overcomes the difficulties encountered by the limited supply of tissue from humans.

BRIEF DESCRIPTION OF THE DRAWINGS

FIG. 4 shows the effect of different M17 treatment schedules on BALB/c ear-heart allograft survival in C3H recipient mice presensitized to BALB/c alloantigens. The squares are rat IgG2a isotype control, and the circles are M17, where solid is days −7 to −3, shaded is days −7 to 13, and open is days 0 to 13.

DESCRIPTION OF THE PREFERRED EMBODIMENTS

I. Definitions

Figure 1B:
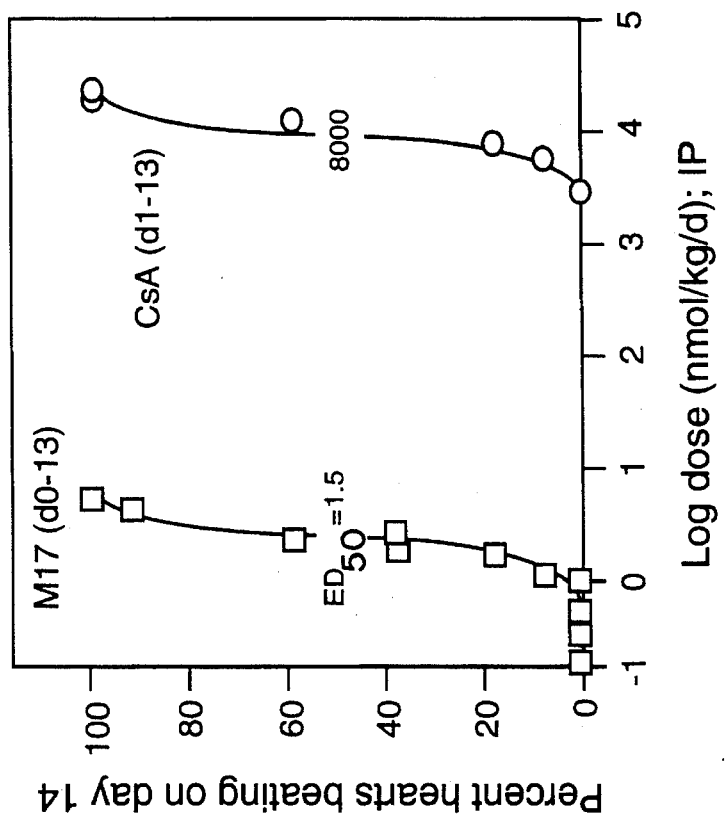
FIGS. 1A and 1B illustrate the comparative efficacies and potencies, respectively, of treatment with M17 (anti-CD11a MAb, stars) and cyclosporin A (CsA, circles) days 1–13 for the prolongation of heterotopic (ear-pinnae), nonprimarily vascularized BALB/c heart graft survival in C3H mouse recipients.

The term "LFA-1-mediated disorders" refers to pathological states caused by cell adherence interactions involving the LFA-1 receptor on lymphocytes. Examples of such disorders include T cell inflammatory responses such as inflammatory skin diseases including psoriasis; responses associated with inflammatory bowel disease (such as Crohn's disease and ulcerative colitis); adult respiratory distress syndrome; dermatitis; meningitis; encephalitis; uveitic; allergic conditions such as eczema and asthma and other conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; diseases involving leukocyte diapedesis; CNS inflammatory disorder, multiple organ injury syndrome secondary to septicaemia or trauma; autoimmune haemolytic anemia; myethemia gravis; antigen-antibody complex mediated diseases; all types of transplantations, including graft vs. host or host vs. graft disease; etc.

"Treating" such diseases includes therapy, prophylactic treatment, prevention of rejection of grafts, and induction of tolerance of grafts on a long-term basis.

"Initial" dosing means dosing that is not the last dosing administered in the treatment and means dosing administered before and/or at the time that the disorder is first incurred (or first apparent or first diagnosed), e.g., the day when transplantation of a graft occurs, preferably at least at the time when the disorder is first incurred, apparent, or diagnosed. The initial dosing need not be a single dose, but it is not the last dose. "Subsequent" dosing is dosing that follows the initial dosing and includes the last dose administered for the treatment. This latter dosing is a maintenance dose ordinarily not sufficient alone to tolerate a second graft.

The term "graft" as used herein refers to biological material derived from a donor for transplantation into a recipient. Grafts include such diverse material as, for example, isolated cells such as islet cells, tissue such as the amniotic membrane of a newborn, bone marrow, hematopoietic precursor cells, and organs such as skin, heart, liver, spleen, pancreas, thyroid lobe, lung, kidney, tubular organs (e.g., intestine, blood vessels, or esophagus), etc. The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. Preferably the graft is bone marrow or an organ such as heart and the donor of the graft and the host are matched for HLA class II antigens.

The term "mammal" refers to any animal classified as a mammal, including humans, domestic and farm animals, and zoo, sports, or pet animals, such as dogs, horses, cats, cows, etc. Preferably, the mammal herein is human.

The term "mammalian host" as used herein refers to any compatible transplant recipient. By "compatible" is meant a mammalian host that will accept the donated graft. Preferably, the host is human. If both the donor of the graft and the host are human, they are preferably matched for HLA class II antigens so as to improve histocompatibility, The term "donor" as used herein refers to the mammalian species, dead or alive, from which the graft is derived, Preferably, the donor is human. Human donors are preferably volunteer blood-related donors that are normal on physical examination and of the same major ABO blood group, because crossing major blood group barriers possibly prejudices survival of the allograft. It is, however, possible to transplant, for example, a kidney of a type O donor into an A, B or AB recipient.

The term "transplant" and variations thereof refers to the insertion of a graft into a host, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, such as a baboon heart transplanted into a human recipient host, and including animals from phylogenically widely separated species, for example, a pig heart valve, or animal beta islet cells or neuronal cells transplanted into a human host.

The term "LFA-1 antagonist" generally refers to an antibody directed against either CD11a or CD18 or both, but also includes ICAM-1, soluble forms of ICAM-1 (e.g., the ICAM-1 extracellular domain, alone or fused to an immunoglobulin sequence), antibodies to ICAM-1, and fragments thereof, or other molecules capable of inhibiting the interaction of LFA-1 and ICAM-1.

The term "anti-LFA-1 antibody" or "anti-LFA-1 MAb" refers to an antibody directed against either CD11a or CD18 or both. The anti-CD11a antibodies include, e.g., MHM24 [Hildreth et al., *Eur. J. Immunol.*, 13: 202–208 (1983)], R3.1 (IgG1) [R. Rothlein, Boehringer Ingelheim Pharmaceuticals, Inc., Ridgefield, CT], 25-3 (or 25.3), an IgG1 available from Immunotech, France [Olive et al., in Feldmann, ed., *Human T cell Clones. A new Approach to Immune Regulation*, Clifton, N.J., Humana, 1986 p. 173], KBA (IgG2a) [Nishimura et al., *Cell. Immunol.*, 107: 32 (1987); Nishimura et al., ibid., 94: 122 (1985)], M7/15 (IgG2b) [Springer et al., *Immunol. Rev.*, 68: 171 (1982)], IOT16 [Vermot Desroches et al., *Scand. J. Immunol.*, 33: 277–286 (1991)], SPVL7 [Vermot Desroches et al., supra], and M17 (IgG2a), available from ATCC, which are rat anti-murine CD11a antibodies.

Examples of anti-CD18 antibodies include MHM23 [Hildreth et al., supra], M18/2 (IgG2a) [Sanches-Madrid et al., *J. Exp. Med.*, 158: 586 (1983)], H52 [Fekete et al., *J. Clin. Lab Immunol.*, 31: 145–149 (1990)], Mas191c [Vermot Desroches et al., supra], IOT18 [Vermot Desroches et al., supra], 60.3 [Taylor et al., *Clin. Exp. Immunol.*, 71: 324–328 (1988)], and 60.1 [Campana et al., *Eur. J. Immunol.*, 16: 537–542 (1986)].

Other examples of suitable LFA-1 antagonists, including antibodies, are described in Hutchings et al., supra, WO 91/18011 published Nov. 28, 1991, WO 91/16928 published Nov. 14, 1991, WO 91/16927 published Nov. 14, 1991, Can. Pat. Appln. 2,008,368 published Jun. 13, 1991, WO 90/15076 published Dec. 13, 1990, WO 90/10652 published Sep. 20, 1990, EP 387,668 published Sep. 19, 1990, EP 379,904 published Aug. 1, 1990, EP 346,078 published Dec.

13, 1989, U.S. Pat. No. 5,071,964, U.S. Pat. No. 5,002,869, Australian Pat. Appln. 8815518 published Nov. 10, 1988, EP 289,949 published Nov. 9, 1988, and EP 303,692 published Feb. 22, 1989.

The antibody is appropriately from any source, including chicken and mammalian such as rodent, goat, primate, and human. Preferably, the antibody is from the same species as the species to be treated, and more preferably the antibody is humanized (i.e., has all human components) and the host is human. While the antibody can be a polyclonal or monoclonal antibody, preferably it is a monoclonal antibody, which can be prepared by conventional technology. The antibody is an IgG-1, -2, -3, or -4, IgE, IgA, IgM, IgD, or an intraclass chimera in which Fv or a CDR from one class is substituted into another class. The antibody may have an Fc domain capable of an effector function or may not be capable of binding complement or participating in ADCC.

The term "immunosuppressive agent" as used herein for adjunct therapy refers to substances that act to suppress or mask the immune system of the host into which the graft is being transplanted. This would include substances that suppress cytokine production, downregulate or suppress self-antigen expression, or mask the MHC antigens. Examples of such agents include 2-amino-6-aryl-5-substituted pyrimidines (see U.S. Pat. No. 4,665,077, supra, the disclosure of which is incorporated herein by reference), azathioprine (or cyclophosphamide, if there is an adverse reaction to azathioprine); bromocryptine; glutaraldehyde (which masks the MHC antigens, as described in U.S. Pat. No. 4,120,649, supra); anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-$\gamma$, -$\beta$, or -$\alpha$ antibodies; anti-tumor necrosis factor-$\alpha$ antibodies; anti-tumor necrosis factor-$\beta$ antibodies; anti-interleukin-2 antibodies and anti-IL-2 receptor antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187 published Jul. 26, 1990), streptokinase; TGF-$\beta$; streptodornase; RNA or DNA from the host; FK506; RS-61443; deoxyspergualin; rapamycin; T-cell receptor (Cohen et al., U.S. Pat. No. 5,114,721); T-cell receptor fragments [Offner et al., Science, 251: 430–432 (1991)]; copending U.S. Ser. No. 07/853,362 filed Mar. 18, 1992, the disclosure of which is incorporated herein by reference; Howell, WO 90/11294; Ianeway, Nature, 341: 482 (1989); and Vandenbark, WO 91/01133]; and T cell receptor antibodies (EP 340,109) such as T10B9. These agents are administered at the same time as or at separate times from the CD11a or CD18 antagonists are used in this invention, and are used at the same dosage as or lesser dosages than as set forth in the art.

The preferred adjunct imunosuppressive agent will depend on many factors, including the type of disorder being treated including the type of transplantation being performed, as well as the patient's history, but a general overall preference is that the agent be selected from cyclosporin A, a glucocorticosteroid (most preferably prednisone or methylprednisolone), OKT-3 monoclonal antibody, azathioprine, bromocryptine, heterologous anti-lymphocyte globulin, or a mixture thereof.

"Increasing tolerance of a transplanted graft" by a host refers to prolonging the survival of a graft in a host in which it is transplanted, i.e., suppressing the immune system of the host so that it will better tolerate a foreign transplant.

"Intermittent" or "periodic" dosing is a dosing that is continuous for a certain period of time and is at regular intervals that are preferably separated by more than one day.

"Selective tolerance" of the disorder refers to a tolerance by the host's immune system for the specific agent causing the disorder, but retaining the ability of the host to reject a second allogeneic or xenogeneic graft. Preferably, the tolerance is such that the immune system is left otherwise intact.

II. Modes for Carrying Out the Invention

Superior immunosuppressive efficacy is seen with a treatment regimen that uses early induction with a high dose of LFA-1 antagonist followed by extended treatment with a lower dose of antagonist.

If antibodies are employed as the antagonist, they are prepared by any suitable technique. LFA-1 or either of its $\alpha$ or $\beta$ chains or any other appropriate immunogen may be used to induce the formation of anti-LFA-1 or anti-ICAM antibodies, which are identified by routine screening. Such antibodies may either be polyclonal or monoclonal antibodies, or antigen binding fragments of such antibodies (such as, for example, F(ab) or F(ab)$_2$ fragments). The antibodies are monovalent or polyvalent for LFA-1 or ICAM-1, and are monospecific for LFA-1 or ICAM-1 or are polyspecific for LFA-1 or ICAM-1 and a predetermined antigen. An LFA-1 antagonist is used in a single course of therapy, different antagonists are used at different stages in therapy (e.g., the initial or sustaining dose), or mixtures thereof are employed (e.g., antibodies to ICAM-1 and to LFA-1).

Polyclonal antibodies to LFA-1 or ICAM-1 generally are raised in animals by multiple subcutaneous (s.c.) or intraperitoneal (i.p.) injections of the CD11a or CD18 polypeptide or dimer thereof or ICAM-1, together with an adjuvant. It may be useful to conjugate the LFA-1 or ICAM-1 antigen polypeptide (including its chains and fragments containing the target amino acid sequence) to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are different alkyl groups.

The route and schedule for antibody stimulation of the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 µg of conjugate (for rabbits or mice, respectively) with 3 volumes of Freund's complete adjuvant and injecting the solution intradermally at multiple sites. One month later the animals are boosted with 1/5 to 1/10 the original amount of conjugate in Freund's incomplete adjuvant (or other suitable adjuvant) by subcutaneous injection at multiple sites. Seven to 14 days later animals are bled and the serum is assayed for antibody titer. Animals are boosted until the titer plateaus. Preferably, the animal is boosted with the conjugate of the same LFA-1 or ICAM polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering immune cells—typically spleen cells or lymphocytes from lymph node tissue—from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.*, 6: 511 (1976) and also described by Hammerling et al., In: *Monoclonal Antibodies and-T-Cell Hybridomas*, Elsevier, N.Y., pp. 563–681 (1981) has been widely applied to produce hybrid cell lines that secrete high levels of monoclonal antibodies against many specific antigens.

It is possible to fuse cells of one species with another. However, it is preferable that the source of the immunized antibody-producing cells and the myeloma be from the same species.

The hybrid cell lines can be maintained in culture in vitro in cell culture media. The cell lines producing the antibodies can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are sterile filtered.

While routinely mouse monoclonal antibodies are used, the invention is not so limited; in fact, human antibodies may be used and may prove to be preferable. Such antibodies can be obtained by using human hybridomas (Cote et al., *Monoclonal Antibodies and Cancer Therapy*, Alan R. Liss, p. 77 [1985]). In fact, according to the invention, techniques developed for the production of chimeric antibodies (Morrison et al., *Proc. Natl. Acad Sci.*, 81: 6851 [1984]; Neuberger et al., *Nature*, 312: 604 [1984]; Takeda et al., *Nature*, 314: 452 [1985]; EP 184,187; EP 171,496; EP 173,494; PCT WO 86/01533; Shaw et al., *J. Nat Canc Inst.*, 80: 1553–1559 [1988]; Morrison, *Science*, 229: 1202–1207 [1985]; and Oi et al., *BioTechniques*, 4: 214 [1986]) by splicing the genes from a mouse antibody molecule of appropriate antigen specificity together with genes from a human antibody molecule of appropriate biological activity (such as ability to bind ICAM-1) can be used; such antibodies are within the scope of this invention.

Techniques for creating recombinant DNA versions of the antigen-binding regions of antibody molecules (known as Fab fragments), which bypass the generation of monoclonal antibodies, are encompassed within the practice of this invention. One extracts antibody-specific messenger RNA molecules from immune system cells taken from an immunized animal, transcribes these into complementary DNA (cDNA), and clones the cDNA into a bacterial expression system. One example of such a technique suitable for the practice of this invention was developed by researchers at Scripps/Stratagene, and incorporates a proprietary bacteriophage lambda vector system that contains a leader sequence that causes the expressed Fab protein to migrate to the periplasmic space (between the bacterial cell membrane and the cell wall) or to be secreted. One can rapidly generate and screen great numbers of functional Fab fragments for those that bind the antigen. Such LFA-1- or ICAM-binding molecules (Fab fragments with specificity for the LFA-1 or ICAM polypeptide) are specifically encompassed within the term "antibody" as it is defined, discussed, and claimed herein.

Typically, the LFA-1 antagonist used in the method of this invention is formulated by mixing it at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of antagonist, but preferably ranges anywhere from about 3 to about 8. Formulation in an acetate buffer at pH 5 is a suitable embodiment.

The LFA-1 antagonist for use herein is preferably sterile. Sterility is readily accomplished by sterile filtration through (0.2 micron) membranes. LFA-1 antagonist ordinarily will be stored as an aqueous solution, although lyophilized formulations for reconstitution are acceptable.

The antagonist composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of LFA-1 antagonist to be administered will be governed by such considerations, and is the minimum amount necessary to prevent, ameliorate, or treat the LFA-1-mediated disorder, including treating rheumatoid arthritis, reducing inflammatory responses, inducing tolerance of imunostimulants, preventing an immune response that would result in rejection of a graft by a host or vice-versa, or prolonging survival of a transplanted graft. Such amount is preferably below the amount that is toxic to the host or renders the host significantly more susceptible to infections.

As a general proposition, the initial pharmaceutically effective amount of the LFA-1 antagonist administered parenterally per dose will be in the range of about 0.1 to 20 mg/kg of patient body weight per day, with the typical initial range of LFA-1 antagonist used being 0.3 to 15 mg/kg/day.

As noted above, however, these suggested amounts of antibody are subject to a great deal of therapeutic discretion. The key factor in selecting an appropriate dose and scheduling is the result obtained, as indicated above. For example, relatively higher doses may be needed initially for the treatment of ongoing and acute graft rejection, or at a later stage for the treatment of acute rejection, which is characterized by a sudden decline in graft function.

Where the subsequent dosing is less than 100% of initial dosing, it is calculated on the basis of daily dosing. Thus, for example, if the dosing regimen consists of daily injections of 2 mg/kg/day for 2 weeks followed by a biweekly dose of 0.5 mg/kg/day for 99 days, this would amount to a subsequent dose of about 1.8% of the initial dose, calculated on a daily basis (i.e., 2/day/100%=0.5/14 days/x%, x=~1.8%). Preferably, the subsequent dosing is less than about 50%, more preferably, less than about 25%, more preferably, less than about 10%, still more preferably, less than about 5%, and most preferably, less than about 2% of the initial dosing of LFA-1 antagonist.

To obtain the most efficacious results, depending on the disorder, the initial dosing is given as close to the first sign, diagnosis, appearance, or occurrence of the disorder as possible or during remissions of autoimmune disorders. Preferably the initial dosing begins before exposure to antigen, as in the case with transplanted grafts. Furthermore, when the initial dosing is prior to or substantially contemporaneous with exposure to antigen, it is preferred that the subsequent dosing is carried out for a longer period of time than the initial dosing, particularly for transplants, and that it be a continuous intermittent maintenance dose that need not be continuous for the life of the patient.

The preferred scheduling is that the initial dosing (i.e., administered before or at the time of the undesired immune response at a dose administered no less frequently than daily up to and including continuously by infusion) and the subsequent dosing is a dose administered periodically no more than about once a week. More preferably, depending on the specific disorder, and particularly for transplantation, the initial daily dosing is administered for at least about one week, preferably at least about 2 weeks, after the exposure to antigen, e.g., graft, or initiation of an acute immune response (as in autoimmune disorders), and the subsequent dosing is administered no more than once biweekly (preferably once biweekly) for at least about 5 weeks, preferably for at least about 10 weeks, after the initial dosing is terminated.

In another preferred embodiment, particularly if the antagonist is anti-CD11a or anti-CD18 antibodies, initial dosing terminates from about 1 day to 4 weeks after transplantation has occurred, more preferably from about 1 week to 3 weeks, more preferably from about 2 weeks to 3 weeks, and commences from about 1 week before transplantation occurs up to about simultaneously with the transplantation.

The LFA-1 antagonist is administered by any suitable means, including parenteral, subcutaneous, intraperitoneal, intrapulmonary, and intranasal, and, if desired for local immunosuppressive treatment, intralesional administration (including perfusing or otherwise contacting the graft with the antagonist before transplantation). Parenteral infusions include intramuscular, intravenous, intraarterial, intraperitoneal, or subcutaneous administration. In addition, the LFA-1 antagonist is suitably administered by pulse infusion, particularly with declining doses of the LFA-1 antagonist. Preferably the dosing is given by injections, most preferably intravenous or subcutaneous injections, depending in part on whether the administration is brief or chronic.

The LFA-1 antagonist need not be, but is optionally formulated with one or more agents currently used to prevent or treat the disorder in question. For example, in rheumatoid arthritis, the antibody may be given in conjunction with a glucocorticosteroid. In addition, T cell receptor peptide therapy is suitably an adjunct therapy to prevent clinical signs of autoimmune encephalomyelitis. Offner et al., supra. For transplants, the antibody may be administered concurrently with or separate from an immunosuppressive agent as defined above, e.g., cyclosporin A, to modulate the immunosuppressant effect. The effective amount of such other agents depends on the amount of LFA-1 antagonist present in the formulation, the type of disorder or treatment, and other factors discussed above. These are generally used in the same dosages and with administration routes as used hereinbefore or about from 1 to 99% of the heretofore employed dosages.

The various autoimmune disorders described above are treated with LFA-1 antagonists in such a fashion as to induce immune tolerance to the self antigen under attack as a result of the disorder. In this regard, autoimmune disorders resemble host versus graft rejection and are treated with LFA-1 antagonists in analogous fashion. However, in these disorders the patient is already mounting an immune response to the target antigen, unlike the case with transplants prior to grafting. Thus, it is desirable to first induce and maintain a transient state of immunosuppression by conventional methods in such patients, e.g. by the conventional use of cyclosporin A or other conventional immunosuppressive agents (alone or together with LFA-1 antagonist), or to monitor the patient until the occurrence of a period of remission (an absence or substantial lessening of pathological or functional indicia of the autoimmune response).

Preferably, transient immunosuppression is induced by T cell depletion using conventional therapy, e.g. as described further in Example 1. This is then followed by the administration of the LFA-1 antagonist in order to prevent rebound when the immunosuppressive inducing agent is withdrawn or when remission otherwise would abrogate. Alternatively, the remission patient's condition is closely monitored for signs of flare, and immediately upon the initial functional or biochemical appearance of flare the initial dosing regimen is started and continued until the flare subsides. The LFA-1 administration during this period constitutes the initial dose described elsewhere herein.

In the case of autoimmune disorders the initial dose will extend about from 1 week to 16 weeks. Thereafter, the lower dose maintenance regimen of LFA-1 antagonist is administered in substantially the same fashion as set forth herein for the amelioration of graft or host rejection, although in some instances it is desirable to extend the subsequent or sustaining dose for lengthier periods than with grafts. In an embodiment of this invention, if an antigen or a composition containing the antigen is known to be responsible for the autoimmune response then the antigen is administered to the patient (optionally with IL-1 and/or gamma interferon) after the initial LFA-1 antagonist dose and the antagonist dose maintained thereafter in order to suppress the regeneration of an autoimmune response against the antigen while minimally immunosuppressing the patient's response to other antigens.

The patient optimally will be isolated, preferably in an aseptic environment such as is currently used in transplant practice, at the time of initial treatment with LFA-1 antagonist. The patient should be free of any infection. It is not necessary to sustain these conditions during the maintenance dose, and in fact this is one of the advantages of this invention, i.e., that the patient is able to mount a substantially normal immune response to ambient antigens (other than the graft or self antigen) while being treated with the maintenance dosing.

The invention herein is particularly amenable to prolonging survival and increasing tolerance of transplanted grafts. The transplants are optionally functionally monitored systematically during the critical postoperative period (the first three months) using any suitable procedure. One such procedure is radionuclide intravenous angiography using 99Tcm-pertechnetate, as described by Thomsen et al., *Acta Radiol.*, 29: 138–140 (1988). In addition, the method herein is amenable to simultaneous, multiple organ perfusion and transplantation (Toledo-Pereyra and MacKenzie, *Am. Sur.*, 46: 161–164 (1980).

In some instances, it is desirable to modify the surface of the graft so as to provide positively or negatively charged groups, as by using a suitable amino acid or polymer or by attaching a physiologically acceptable source of charged functional groups. For example, a negatively charged surface is appropriate for blood vessels to diminish blood clotting. It also is desirable in certain circumstances to render the surface hydrophobic or hydrophilic by coupling, e.g., phenylalanine, serine or lysine to the surface. An immunosuppressive agent particularly effective for these surface modifications is glutaraldehyde.

As mentioned above, before transplantation an effective amount of the antibody is optionally administered to induce tolerance of the graft. The same dose and schedule as used for initial post-transplantation may be employed. Furthermore, prior to transplantation the graft is optionally contacted with a TGF-β composition as described in U.S. Pat. No. 5,135,915, the disclosure of which is incorporated by reference. Briefly, the contact suitably involves incubating or perfusing the graft with the composition or applying the composition to one or more surfaces of the graft. The treatment generally takes place for at least one minute, and preferably from 1 minute to 72 hours, and more preferably from 2 minutes to 24 hours, depending on such factors as the concentration of TGF-β in the formulation, the graft to be treated, and the particular type of formulation. Also as noted, the graft is simultaneously or separately perfused with LFA-1 antagonist. Perfusion is accomplished by any suitable procedure. For example, an organ can be perfused via a device that provides a constant pressure of perfusion having a pressure regulator and overflow situated between a pump and the organ, as described by DD 213,134 published Sept. 5, 1984. Alternatively, the organ is placed in a hyperbaric chamber via a sealing door and perfusate is delivered to the chamber by a pump that draws the fluid from the reservoir while spent perfusate is returned to the reservoir by a valve, as described in EP 125,847 published Nov. 21, 1984.

After the graft is treated, it is suitably stored for prolonged periods of time or is used immediately in the transplant procedure. Storage life can be enhanced as described above by using a blood substitute in the formulation (e.g., perfluorochemical emulsion), or by perfusing the graft with a formulation of a TGF-β containing chilled isotonic agent and anticoagulant followed by glycerol to allow for freezing of removed organs with no destruction of the cells, as described in JP 60061501 published Apr. 9, 1985. In addition, the organs can be preserved with known perfusion fluids (containing TGF-β and/or LFA-1 antagonist as noted) while the organs are cooled to freezing temperatures, to preserve the organ semi-permanently without cell necrocytosis, as described by U.S. Pat. Nos. 4,462,215 and 4,494,385.

Respecting cardiac transplants specifically, Parent et al., *Cryobiology*, 18: 571–576 (1981) reports that cold coronary perfusion prior to transplantation at 5° C. increases protection of the homograft during the initial period of implantation. Any of these procedures, or others, are within the scope of this invention if deemed necessary for graft preservation.

Before transplantation, the graft is preferably washed free of the TGF-β composition, as by soaking it in a physiological saline solution or by other means appropriate for this purpose. It is not desirable to remove the LFA-1 antagonist prior to transplantation.

Also, prior to transplantation, the host is optionally given one or more donor-specific blood transfusions to aid in graft survival. An alternative procedure is to subject the host to total lymphoid irradiation prior to or after the transplantation operation. Any other pre-transplant procedures that would be beneficial to the particular transplant recipient can be performed as part of the method of this invention.

The invention will be more fully understood by reference to the following examples. They should not, however, be construed as limiting the scope of the invention. All literature citations are incorporated by reference.

EXAMPLE 1

Murine Heart Graft Model using anti-CD11a Antibody

Neonatal BALB/c ($H-2^d$) hearts were transplanted into the dorsal ear pinnae of male adult (8 to 10 weeks old) C3H ($H-2^k$) mice as described in Babany et al., *J. Pharmacol. Exp. Ther.*, 244: 259 (1988). All mice were raised under specific pathogen-free conditions and were obtained from the Department of Comparative Medicine, Stanford University Medical Center. The reagents employed were M17 (clone M17/4.411.9, rat IgG2a anti-murine CD11a MAb purified from ascites, obtainable from the American Type Culture Collection, Rockville, Md. (ATCC Accession No. TIB 217), cyclosporin A (CsA; i.v. formulation, Sandoz, East Hanover, N.J.), or IgG2a (rat isotype control, Zymed. S. San Francisco, Calif.). M17 (n=3–9/dose group) or CsA (n=5–20/dose group) was administered to the mice daily i.p. for two weeks starting on the day of transplantation (M17) or on the first post-transplant day (CsA).

Figure 1A:
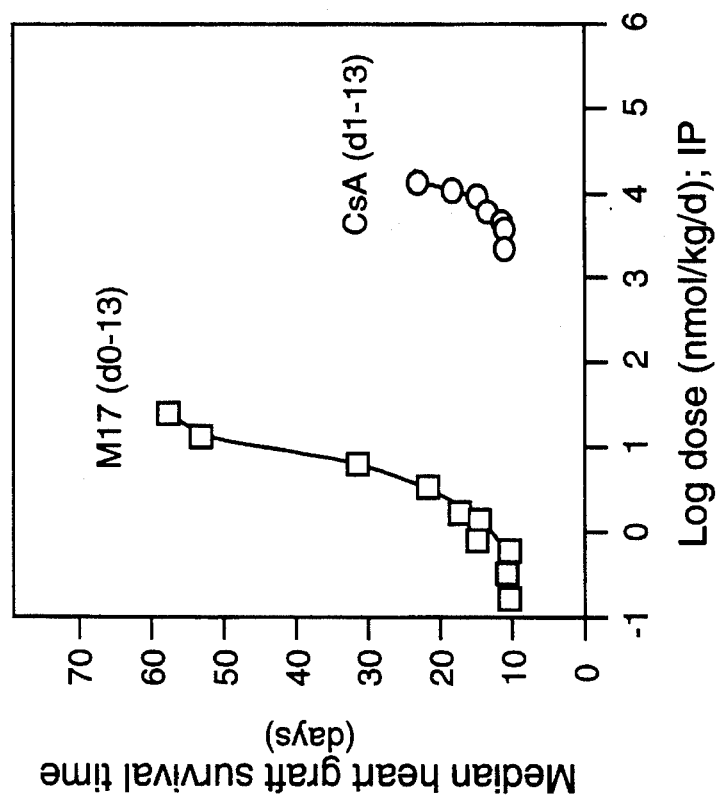

The results are shown in FIGS. 1A and 1B, representing efficacy and potency, respectively. Grafts in untreated (n=105) or in rat IgG2a isotype control-treated (n=9) mice were rejected in 10.63±0.1 days (median graft survival time [MST]±S.E.; median survival=10.0 days) and 10.0±0.3 days (median survival=10.0 days), respectively. Compared to CsA, M17 prolonged graft survival much more effectively and potently. The MST of mice treated with 4 mg/kg/day M17 was extended to 58 days, whereas the MST was only 24 days in mice treated with a maximally tolerated dose (25 mg/kg/day) of CsA (FIG. 1A). In fact, 2 mg/kg/day M17 prolonged graft survival significantly more than 25 mg/kg/day CsA ($p<0.05$). The highest M17 dose (4 mg/kg/day) administered produced no observable toxicity.

To compare quantitatively the relative imunosuppressive potencies of M17 and CsA to obtain dose-response curves for immunosuppression, a quantal in vitro murine heart allograft bioassay was used. Morris, *Transplant Rev.*, 6: 39 (1992). For each dose group, the mean percent beating heart allografts on day 14 as a function of $\log_{10}$ dose was fit by logistic regression. When the $ED_{50}$s of M17 and CsA were compared (the doses are expressed as nmol/kg to control for the difference in molecular weight between these two drugs), M17 was approximately 5000 times more potent than CsA. (The $ED_{50}$s for M17 and CsA were 1.48 nmol/kg and 8.10 μmole/kg, respectively.) See FIG. 1B. There is a dramatic disparity between the potency of M17 and CsA.

Figure 2:
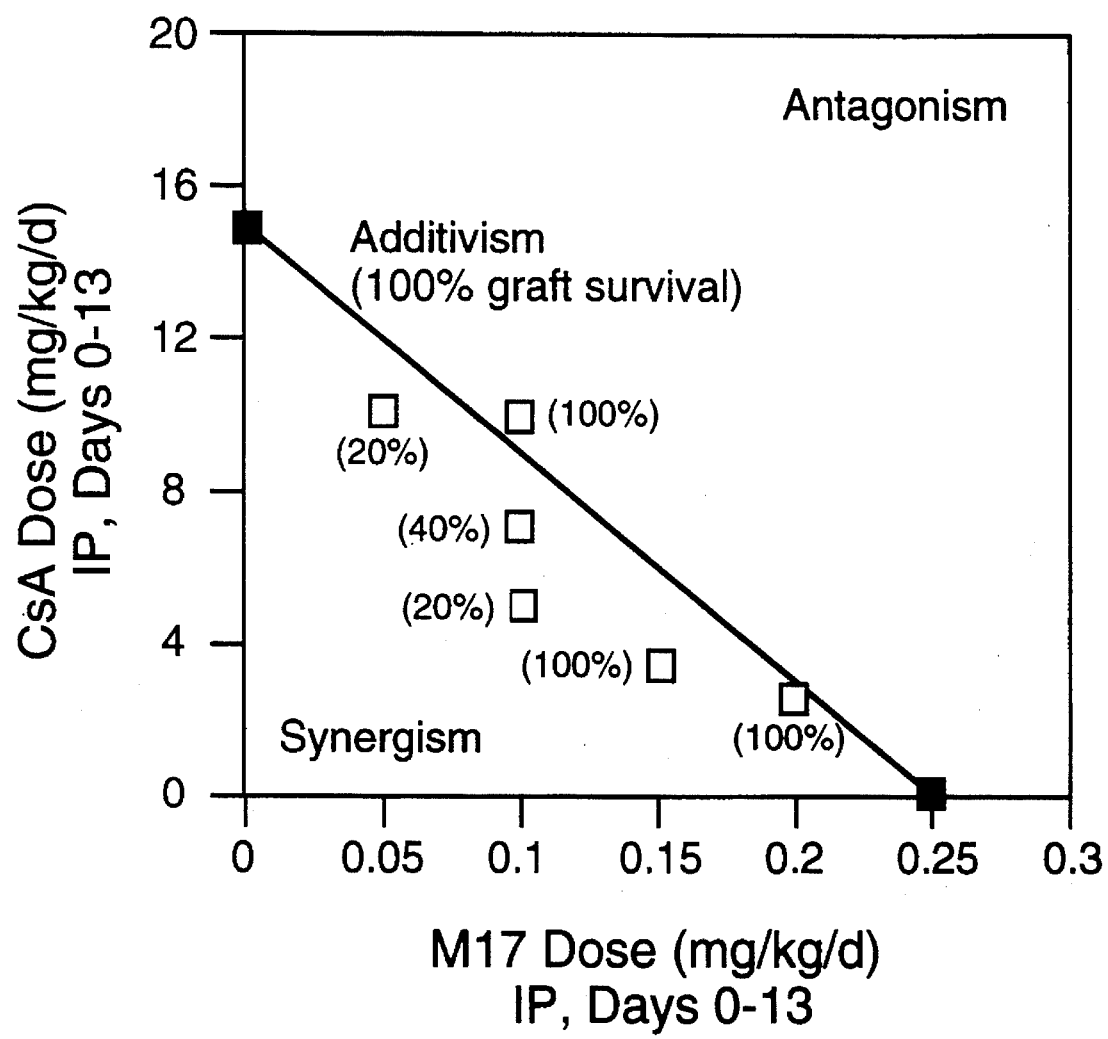
FIG. 2 is an isobologram plot of data derived from the quantal BALB/c to C3H mouse heart graft bioassay. This assay was used to evaluate the effect of combined daily treatment with different doses of M17 and CsA (n=5/dose group) on graft survival. The percent viable grafts on post-transplant day 14 was used as the endpoint of the assay.

Since it is likely that any new immunosuppressive agent initially will be used clinically in combination with CsA, different doses of M17 and CsA were administered in combination for two weeks to C3H recipients of BALB/c heart grafts. To determine whether M17 and CsA interact to produce immunosuppression that is antagonistic, additive, or synergistic, isobologram analysis was used to evaluate graft survival data. According to the geometric isobologram method described by Berenbaum, *Pharmacol. Rev*, 41: 93 (1989), the additivism isobole is defined as the line joining the minimum M17 and CsA doses required for 100% graft survival. FIG. 2 shows that M17 and CsA do not interact antagonistically; rather, combined treatment with M17 and CsA produced 100% graft survival at doses that are predicted if these drugs interact additively.

Figure 3:
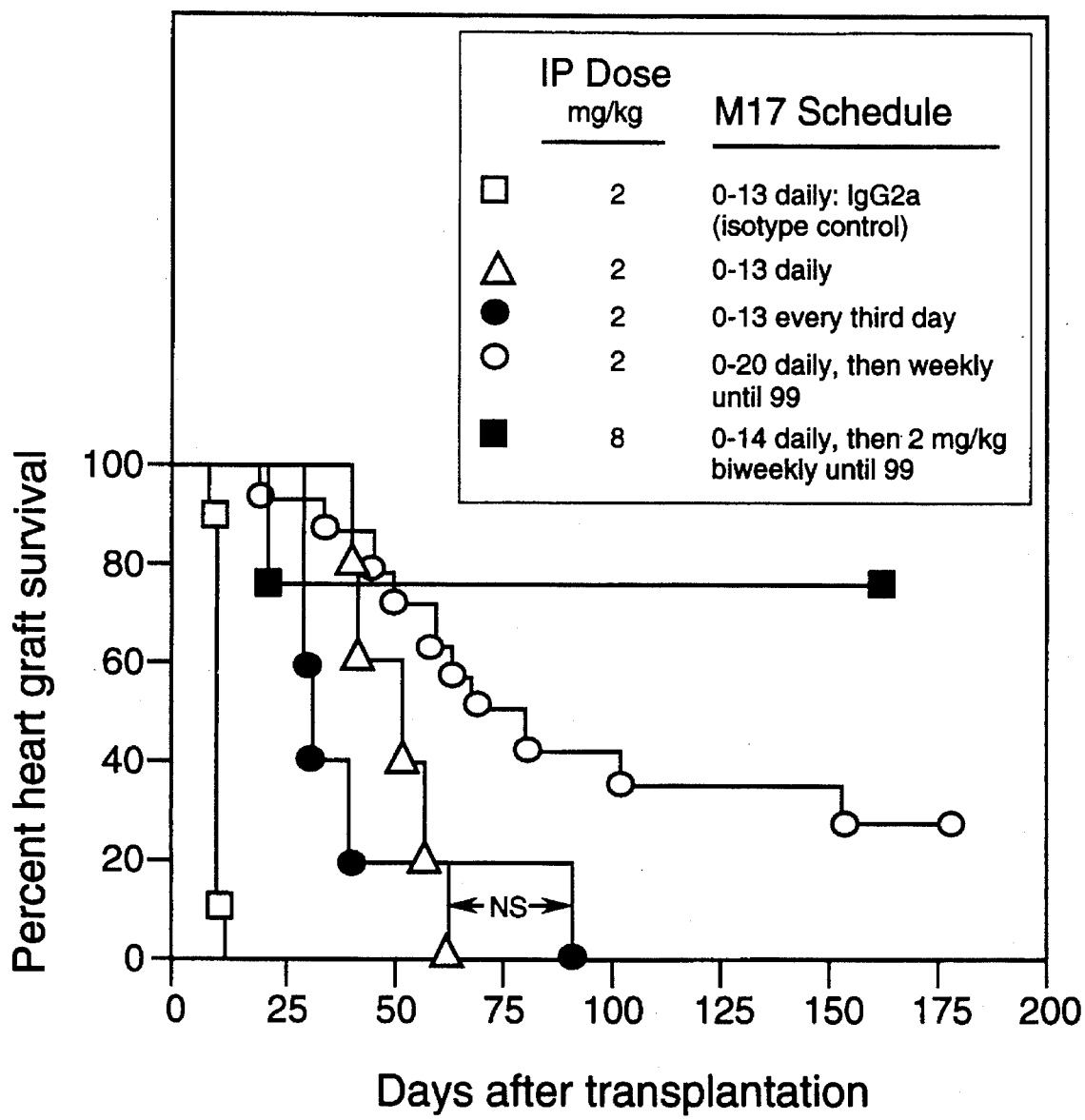
FIG. 3 shows the effect of M17 dose (intraperitoneal, i.p.) and schedule on the survival of heterotopic (ear-pinnae), nonprimarily vascularized BALB/c heart grafts in C3H mouse recipients (n=4–14/group). The Mann-Whitney U test was used to determine levels of statistical significance (corrected for small sample sizes) for the differences in survival times between groups. $p > 0.05$ was considered not significant (NS). The open circles are 2 mg/kg of rat IgG2a isotype control 0–13 days daily, the solid squares are 2 mg/kg of M17 0–13 days daily, the solid circles are 2 mg/kg of M17 0–13 days every third day, the triangles are 2 mg/kg of M17 0–20 days daily, then weekly until day 98, and the stars are 8 mg/kg of M17 0–14 days daily, then 2 mg/kg biweekly until day 99.

To determine whether treatment with M17 for more than two weeks increases graft survival, 2 mg/kg/day of M17 was administered daily for three weeks followed by weekly treatment until day 98 post-transplant. Despite cessation of treatment on day 98, some heart grafts continued to contract for more than 90 additional days (FIG. 3). In another group, recipient mice were treated with 8 mg/kg/day of M17 daily for two weeks followed by biweekly doses of 2 mg/kg until day 99. This treatment regimen substantially increased the number of heart grafts surviving indefinitely compared to mice treated with the lower dose of M17 (FIG. 3). Since treatment in the early post-operative period with 8 mg/kg/day of M17 induced long-term graft survival more effectively than treatment with 2 mg/kg/day, high peri-operative blood levels of M17 may be critical for long-term graft survival.

Because extended treatment with 2 mg/kg/day of M17 produced indefinite graft survival in some recipients, the specificity of this immunosuppression was investigated in these animals by transplanting C57BL/6 ($H-2^b$) heart grafts into their contralateral ear pinnae 154 days after the primary grafts. The primary BALB/c grafts were not rejected even though the C57 grafts were rejected promptly; the MST for C57 grafts was not significantly (p>0.05) different from the MST of C57 grafts transplanted into non-immunosuppressed mice (Table 1). Therefore, limited treatment with M17 did not cause long-term non-specific immunosuppression, since the immune systems in treated mice were fully capable of responding to third-party alloantigens.

TABLE 1

Survival of C57 heart grafts compared to BALB/c primary grafts in C3H mice that accepted primary graft for more than 154 days

| M17 Treatment with 2 mg/kg/day, i.p., day 0–20, then weekly until day 98 | | No treatment | |
| --- | --- | --- | --- |
| BALB/c graft survival (days) | C57 graft survival (days) | C57 graft survival (days) | p value[a] |
| >190 | 7 | 8 | NS |
| >190 | 14 | 11 | |
| >190 | 14 | 11 | |
| >200 | 41 | 14 | |

[a] The Mann-Whitney U test (corrected for small sample sizes) was used to determine the level of statistical difference between C57 graft survival in M17-treated and untreated mice. p > 0.05 was considered not significant (NS).

Normally, prolonged treatment with MAbs elicits a xenogeneic antibody response that limits the therapeutic efficacy of prolonged MAb treatment. Norman, *Sem. Nephrology*, 12: 315 (1992). It was found here, however, that extended treatment with M17 was more effective than brief treatment (FIG. 3). The results herein suggested that the xenogeneic response of mice to M17 differed from the responses to other MAbs. Mouse anti-rat antibodies in the sera of M17-treated mice were determined by an ELISA that used M17 as the capture antibody and was developed with a horseradish peroxidase-conjugated rat anti-mouse IgG antibody. Results of these studies showed that the xenogeneic antibody response was inversely related to the M17 treatment dose. For example, mice treated with 0.25 mg/kg/day of M17 produced an anti-rat immunoglobulin response by day 15, but mice treated for the same time with 4 mg/kg/day of M17 did not respond to rat immunoglobulin.

To characterize further the ability of M17 to suppress graft rejection, a model of accelerated rejection was used. Primary BALB/c hearts were transplanted into C3H recipients to sensitize these mice to BALB/c alloantigens and were removed four days later. Thus, mice (n=5–10/group) were presensitized with temporary BALB/c heterotopic (ear-pinnae), nonvascularized heart grafts from days −7 to −3 at which time the ears bearing these primary grafts were removed. After transplantation of secondary BALB/c heart grafts on day 0, the individual survival times and the MSTs (horizontal lines in FIG. 4) were determined and are shown in FIG. 4 for each treatment group. Levels of statistical significance between graft survival times in the different treatment groups and the control group were computed using the Mann-Whitney U test (corrected for small sample sizes). p>0.05 was considered not significant (NS).

Secondary grafts transplanted into the contralateral ear pinnae of mice treated i.p. with 4 mg/kg of isotype control rat IgG2a from days −7 to 13 all underwent accelerated rejection and failed to beat. See FIG. 4.

Different schedules (relative to the day of primary grafting) were used to administer 4 mg/kg/day of M17 i.p. to recipients. One group of mice was treated with 4 mg/kg/day of M17 from the day on which the primary hearts were grafted until two weeks after transplantation of secondary grafts. The MST of grafts in these mice was 42 days. This schedule and dose of M17 prevented sensitization since the MST of grafts in these mice did not differ significantly (p>0.05) from the MST of grafts in non-sensitized recipients treated with 4 mg/kg/day of M17 for the first two weeks after transplantation. Results from other experiments showed that the timing of M17 treatment was more important than the duration of treatment. The MST of secondary grafts in mice in which treatment with M17 was delayed until the day of secondary heart transplantation was significantly less (p<0.05) than the MST of grafts in non-sensitized mice treated identically with M17. Therefore, M17 treatment did not eliminate alloreactivity once sensitization had occurred.

In other experiments, it was shown that the MST of secondary grafts in mice treated with M17 for only the four days during which the primary grafts were in place was not significantly different (p>0.05) from the MST of secondary grafts in mice treated from the day of primary heart transplantation until two weeks after transplantation of the secondary graft. Thus, M17 needed to be administered only during the period of sensitization to prevent accelerated rejection. The MST of secondary grafts in mice treated with M17 for the four days preceding implantation of the secondary graft was also not significantly (p>0.05) different from the MST of grafts in non-sensitized recipients treated with M17 from day 0–13. Thus, brief pre-treatment with M17 was no less effective than a longer M17 treatment course post-transplant.

Delaying M17 treatment (2 mg/kg/day) until post-transplant day 4 or 6, when severe rejection is evident in untreated mice, prolonged graft survival only slightly over the control (MSTs of 16 and 14 days, respectively). Similarly, others have found that an anti-CD11a MAb does not reverse acute renal allograft rejection in humans. LeMauff et al., supra. These results, along with the in vitro findings of Davignon et al., supra, and the conclusion of Springer et al., *Annu. Rev. Immunol.*, 5: 223 (1987), suggest that treatment early in the immune response is critical for the immunosuppressive efficacy of M17.

The histology of spleens, thymuses, and lymph nodes from mice (n=5) treated with 4 mg/kg/day of M17 for two weeks was determined using flow cytometric studies. Percent total T cells (anti-Thy 1.2-FITC), CD4 (anti-L3T4-PE), and CD8 (anti-Lyt 2-FITC) T cell subsets, B cells (anti-B220-PE; all MAbs from Caltag, S. San Francisco, Calif.), and LFA-1+ (anti-CD11a-FITC, which recognize a different epitope than M17; clone 2D7, Pharmingen, San Diego, Calif.) spleen cells from mice that were untreated or from mice 14 days after daily i.p. treatment with 4 mg/kg of isotype control rat IgG2a or M17 (n=5/group) were determined using a Profile II (Coulter Ejpics, Hialeah, Fla.).

Figure 5:
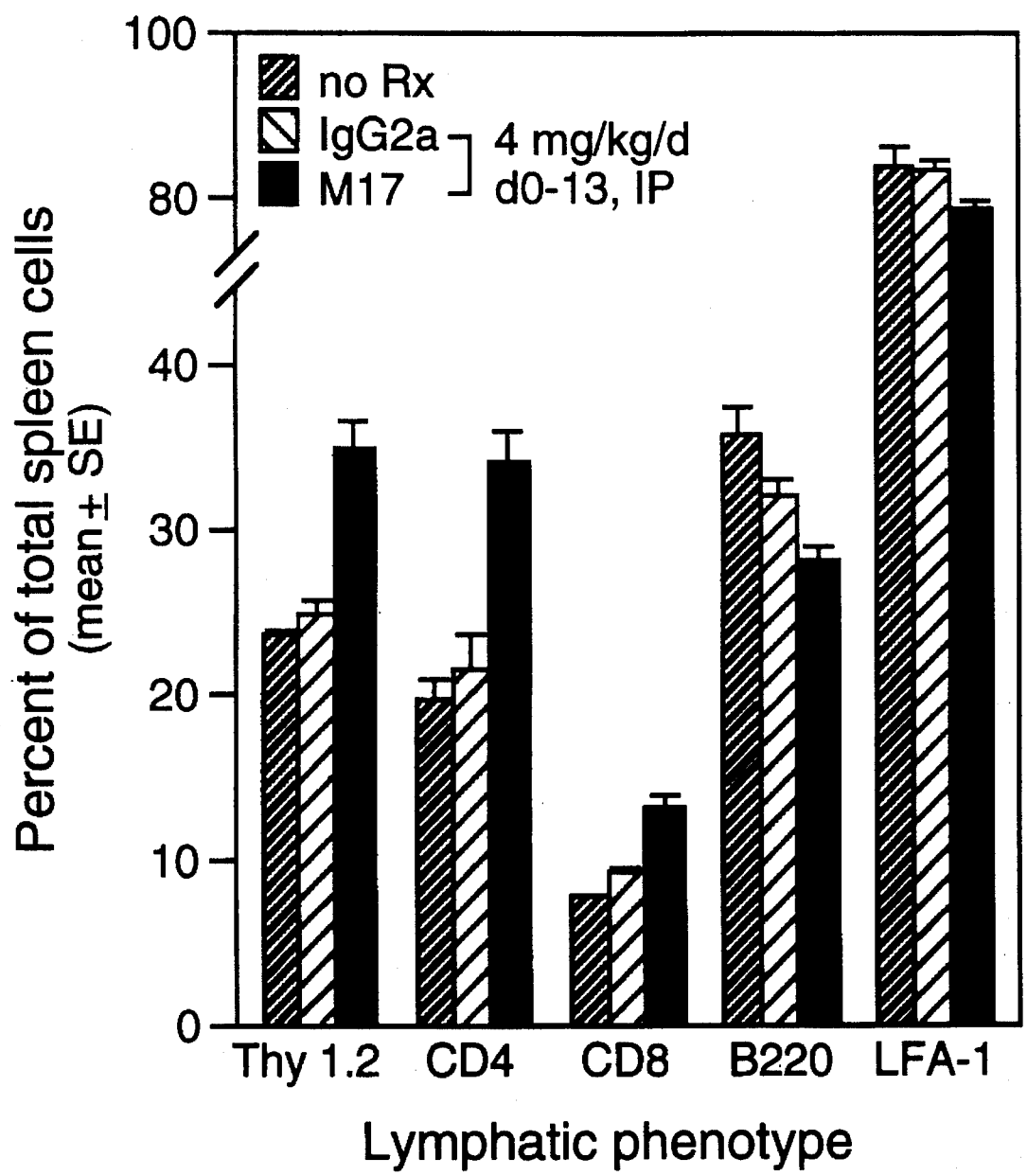
FIG. 5 shows the effect of treatment with M17 on relative proportions of spleen lymphocyte populations determined by flow cytometry. The open bars are no treatment, the shaded bars are treatment with rat IgG2a isotype control, and the solid bars are treatment with M17, where the treatment is 4 mg/kg/day from day 0 to day 13, i. p.

The flow cytometric studies (FIG. 5) showed an increase in percent splenic T cells expressing pan T, CD4, and CD8 markers. Furthermore, the percent of LFA-1+ spleen cells did not differ substantially among M17-, IgG2a-, or non-treated mice. Moreover, there was no evidence of a decrease in yield of leukocytes per spleen in M17-treated mice compared to controls. Therefore, M17 does not appear to cause immunosuppression by central or peripheral lymphoid depletion. Furthermore, complete blood counts in these mice showed that M17 treatment did not suppress the number of lymphocytes compared to IgG2a-treated (n=3) control mice.

Since treatment with M17 does not cause T cell depletion and since the results herein and those of others [Isobe et al., supra] show that LFA-1 is expressed after treatment with anti-LFA-1 MAbs, M17 may cause immunosuppression by functional inactivation of T cells. Thus, the function of immune cells from mice treated daily for two weeks with 4 mg/kg/day of M17 was assessed by determining the proliferative response of spleen cells to ConA in vitro. After 14 days of daily i.p. treatment with 4 mg/kg/day of either isotype control IgG2a (n=5) or M17 (n=5), spleens were removed and cells cultured in KC2000 (Hazelton Biologics, Lenexa, Kans.) in 96-well plates for 3 days with different concentrations of ConA (Vector, Burlingame, Calif.). Cell proliferation was assessed by pulsing with $^3$H-TdR (ICN Radiochemicals, Irvine, Calif., specific activity 6.7 Ci/mM) for 16–18 hours and the $^3$H-TdR incorporation was determined by scintillation spectroscopy (Packard, Downers Grove, Ill.). For each ConA concentration, the mean disintegrations/min (dpm) was computed after subtracting background dpm for cells from control mice and M17-treated mice. The data were expressed as the percent change in dpm in spleen cells from M17-treated mice relative to dpm in spleen cells from control mice. $p>0.05$ determined using the Student's t test was considered not significant (NS).

Figure 6:
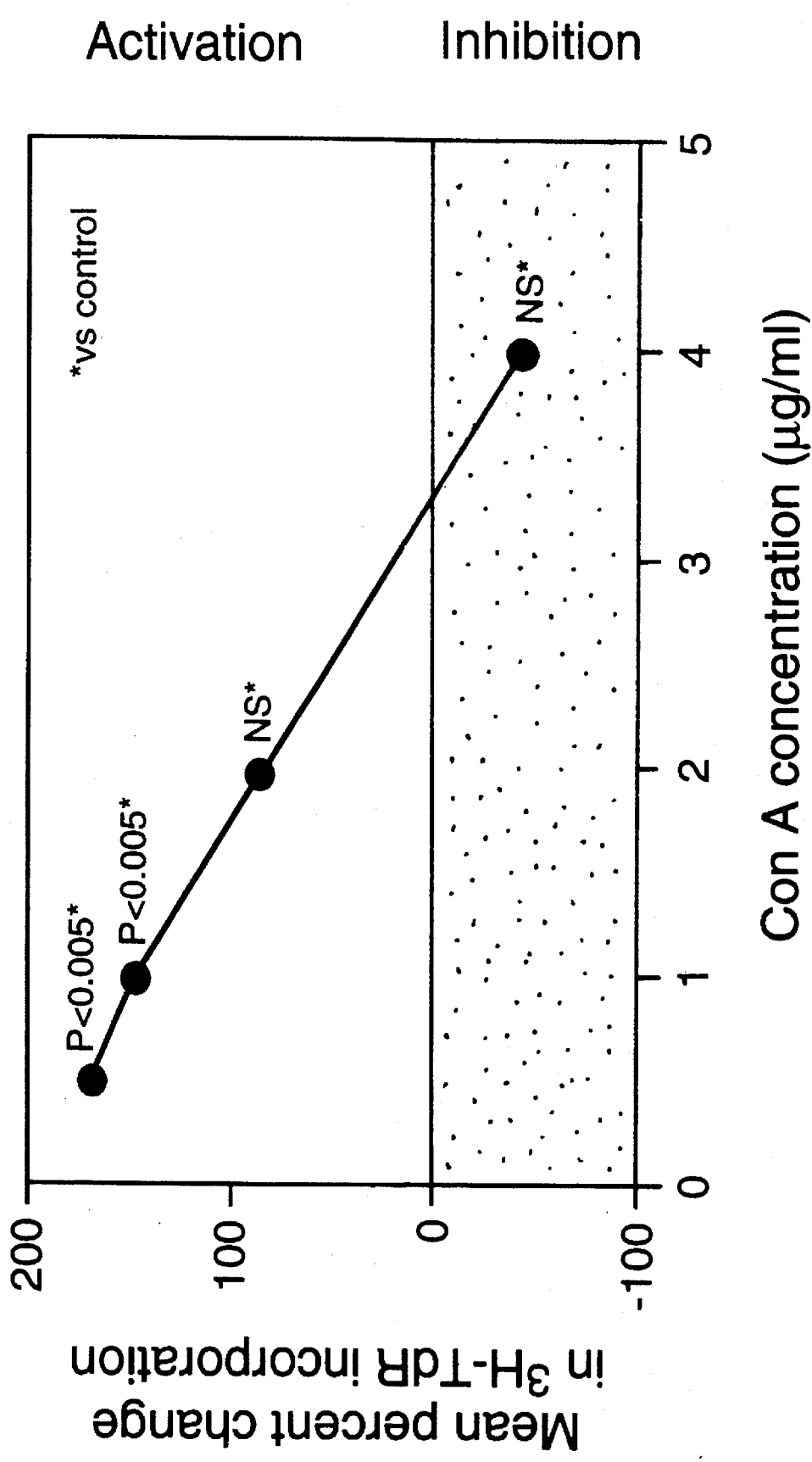
FIG. 6 shows the effect of in vivo treatment with M17 on the in vitro proliferative response of C3H spleen cells to ConA. The shaded portion of the graph of mean percent change in $^3$H-TdR incorporation versus ConA concentration represents inhibition, while the unshaded portion represents activation. The p values are versus the control.

FIG. 6 shows that at low ConA concentrations, the proliferative response of spleen cells from mice treated with M17 was activated 150–200% more than the response of spleen cells from IgG2a-treated control mice. These data show that treatment with M17 does not impair T cell activation.

The host versus graft popliteal lymph node (PLN) hyperplasia assay was used to investigate the mechanisms by which M17 suppresses the response to alloantigens in vivo. On day 0, $2.5 \times 10^6$ irradiated BALB/c spleen cells were injected into each left hind footpad of C3H mice (n=5/group) and the mice were treated immediately with either isotype control IgG2a or with M17 or beginning one or two days after cell injection. On day 4, the right and left PLNs were removed and the mean difference in weight between the left PLNs and right PLNs was determined for each treatment group. Levels of statistical significance of PLN weight differences between M17 treatment groups and the control group were computed using the Mann-Whitney U test (corrected for small sample sizes).

Figure 7:
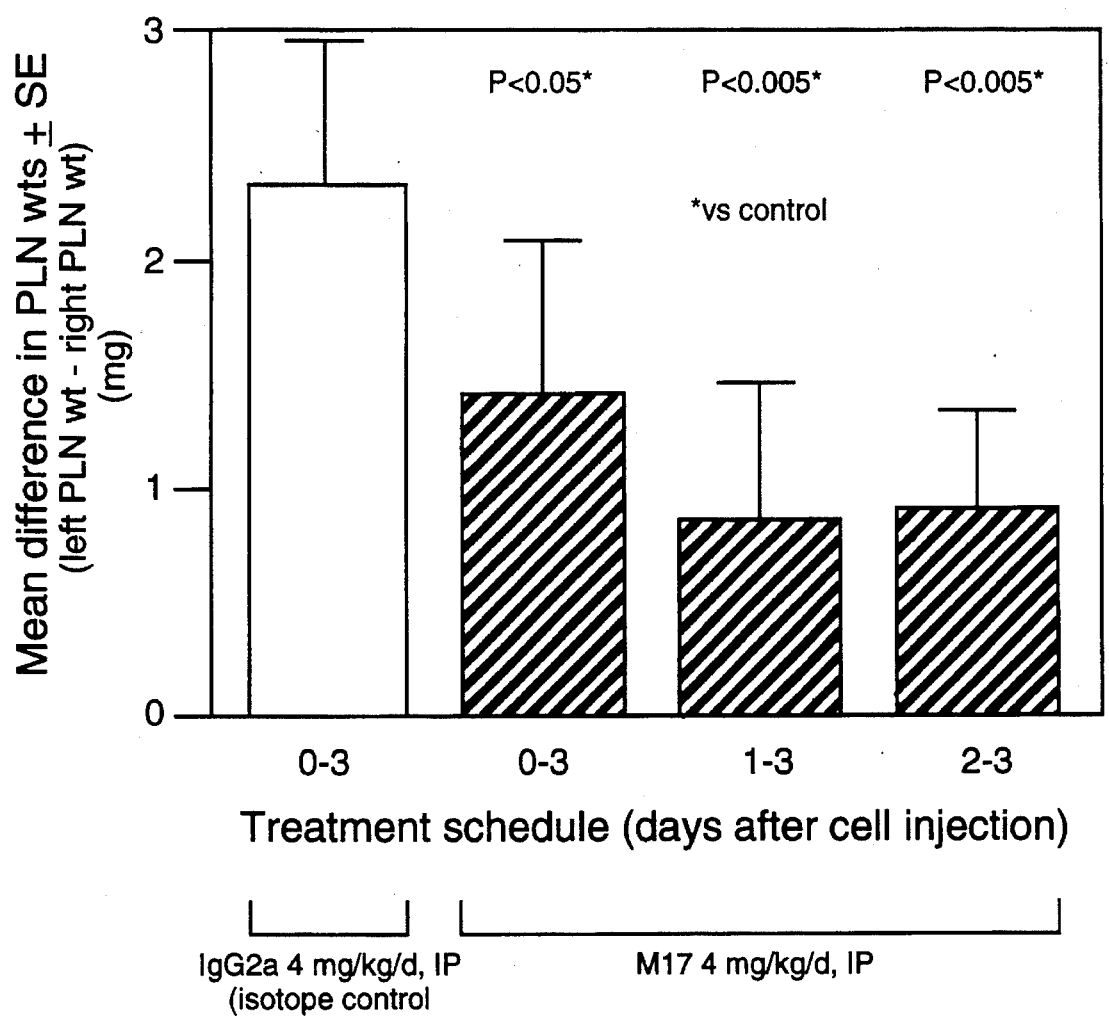
FIG. 7 shows the effect of treatment with M17 on the host versus graft popliteal lymph node (PLN) hyperplasia assay. The p values are versus the control.

The increase in left PLN weights after alloantigenic stimulation in IgG2a-treated control mice as shown in FIG. 7 is caused by cell proliferation and recruitment of lymphoid cells into the PLN due to altered cell migration. Treatment with M17 significantly suppressed increases in PLN weights regardless of whether treatment was begun on day 0 or on day 2. This inhibition could be caused by effects of M17 on the proliferative response to alloantigens or by its effects on lymphocyte trafficking or both. Since others have shown that treatment with anti-CD11a MAb inhibits lymphocyte homing to peripheral lymph nodes in mice [Hamann et al., J. Immunol., 140: 693 (1988)], this effect may be one of the mechanisms by which heart allograft survival is prolonged in M17-treated mice, although this is only one theory and the invention is not limited thereto.

In summary, administration of anti-CD11a antibody at the time of alloantigenic stimulation using a high initial dosing of antibody followed by a lower subsequent dosing produces long-term allograft survival and prevents sensitization to alloantigens in the difficult mouse heterotopic ear-heart model without lymphoid cell depletion. A state of selective unresponsiveness develops: mice that failed to reject their initial grafts reject third party grafts. Since M17 produced long-term graft survival even without the co-administration of anti-ICAM-1 MAb, suppression of the immune system by anti-adhesion molecule MAbs may depend more on blocking the interaction between LFA-1 and ICAM-1 than on preventing the interaction of ICAM-1 with its other receptors, Mac-1 and CD43.

Treatment with anti-CD4 used alone or in combination with total lymphoid irradiation [Trager et al., supra] or with anti-CD3 MAb used alone or in combination with anti-CD2 MAb prolongs allografts far less effectively in this model than M17 treatment despite the substantial T cell depletion or near complete decrease in CD3 cell surface expression these treatments produce. In addition, treatment with M17 is much more effective, far more potent, and has a greater therapeutic index than CsA. The ear-heart model has been used extensively to evaluate other new xenobiotic immunosuppressants and analysis of the data indicates that treatment with M17 for prevention of rejection is more effective and has a higher therapeutic index than mycophenolate mofetil (RS-61443) [Morris et al., Transplant. Proc., 22: 1659 (1990)], brequinar [Murphy and Morris, Med. Sci. Res., 19: 835 (1991)], or FK506 [Morris et al., Transplant. Proc., 22: 1638 (1990)].

EXAMPLE 2

Encephalomyelitis Model Using anti-CD11a Antibody

Experimental autoimmune encephalomyelitis (EAE) is an inflammatory condition of the central nervous system with similarities to multiple sclerosis. In both diseases, circulating leukocytes penetrate the blood-brain barrier and damage myelin, resulting in impaired nerve conduction and paralysis.

EAE is induced in Lewis rats by subcutaneous injection of 50 µg guinea-pig basic protein (GPBP) [Vandenbark et al., Nature, 341: 541 (1989)]+400 µg Mycobacteria in complete Freund's adjuvant (CFA). One group of rats is untreated and one group of rats is injected subcutaneously with 1–10 mg/kg/day daily of M17 mixed with CFA and 100 µg Mycobacteria at either day −4, day −3, day −2, day −1, day 0, day 1, day 2, day 3, day 4, day 5, day 6, day 7, day 8, day 9, day 10, day 11, day 12, or day 13, with day 0 being the day when the GPBP is given. This administration is continued up to day 21. Then, on days 28 and 35, each rat is injected subcutaneously with 0.25–2.5 mg/kg/day of M17 mixed with CFA and 100 μg Mycobacteria. The average onset of EAE in this model is 14 days and average length of paralysis is 6 days. The severity of EAE in the experimental rat model is reduced by administration of the anti-LFA-1 antibody, M17.

In another experiment, pooled groups of B10.PL mice are challenged subcutaneously at the base of the tail with 120 μg of the encephalitogenic MBP 1-9NAc peptide [Urban et al., Cell, 54: 577–592 (1988)] in CFA. At 24 and 74 hours after injection, the mice are injected with $6 \times 10^9$ heat-killed Bordetella pertussis intravenously according to Zamvil et al., Nature, 324: 258–260 (1986). One group of mice is untreated and one group of mice is injected subcutaneously with 1.5-13 mg/kg/day daily of M17 in normal saline at either day −4, day −3, day −2, day −1, day 0, day 1, day 2, day 3, day 4, day 5, day 6, day 7, day 8, day 9, day 10, day 11, day 12, or day 13, with day 0 being the day when MBP peptide is given. This administration is continued up to day 21. Then, on days 28 and 35, each mouse is injected subcutaneously with 0.3–4 mg/kg/day of M17. The mice are observed daily for clinical signs of EAE. The average day of onset for the untreated mice developing EAE in this model is 8–12 days. The severity of EAE in the experimental mouse model is reduced by administration of the anti-LFA-1 antibody, M17.

EXAMPLE 3

In vitro Mixed Lymphocyte Culture Model Using anti-CD18 Antibody

This mixed lymphocyte culture model, which is an in vitro model of transplantation [A.J. Cunningham, "Understanding Immunology," Transplantation Immunology, p. 157–159 (1978)], examines the effects of various α-ICAM, α-LFA-1 antibodies, and soluble ICAM in both the proliferative and effector arms of the human mixed lymphocyte response.

I. Protocol:

A. Mixed Lymphocyte Response

Part 1: Isolation of Cells: Mononuclear cells from peripheral blood (PBMC) were separated from heparinized whole blood drawn from healthy donors. Blood was diluted 1:1 with saline, layered, and centrifuged at 2500×g for 30 minutes on LSM (6.2 g Ficoll and 9.4 g sodium diatrizoate per 100 ml) (Organon Technica, N.J.). Cells were resuspended in RPMI 1640 medium (GIBCO, Grand Island, N.Y.) supplemented with 5% heat-inactivated pooled human AB serum (Peninsula Memorial Blood Bank, Burlingame, Calif.), 1 mM sodium pyruvate, 3 mM L-glutamine, 1 mM nonessential amino acids, 500 μg/ml penicillin, 50 μg/ml streptomycin, 50 μg/ml Gentamycin (GIBCO), and $5 \times 10^5$M 2-mercaptoethanol (Sigma, St. Louis, Mo.).

Part 2: Mixed Lymphocyte Response MLR): One way human mixed lymphocyte cultures were established in 96-well flat-bottomed microtiter plates. Briefly, $1.5 \times 10^5$ responder PBMC in 200 μl of complete medium were co-cultured with an equal number of allogeneic irradiated (3000 rads) stimulator PBMC. Soluble ICAM-1 or anti-integrin antibodies [MHM24 (anti-CD11a) and H52 (anti-CD18), described in the references set forth above] were added at the initiation of cultures. Cultures were incubated at 37° C. in 5% $CO_2$ for 5 days, then pulsed with 1 μCi/well of $^3$H-thymidine (6.7 Ci/mmol, NEN, Boston, Mass.) for 16 hours. Cultures were harvested on a PHD cell harvester (Cambridge Technology, Inc., Watertown, Mass.). [$^3$H]TdR incorporation was measured with a Beckman scintillation counter (LS6800) and triplicate determinations were averaged. Data are expressed as net cpm. The mean [$^3$H]-TdR incorporated by control cultures was <1000 cpm.

B. Cytotoxic T lymphocyte (CTL) Assay:

Part 1: Generation of CTL: (CTLs were generated in a 7-day mixed lymphocyte culture, except cultures were scaled up to generate large numbers of cells.) Peripheral blood lymphocytes from two unrelated donors were isolated with LSM in conventional fashion. Cells were adjusted to $3 \times 10^6$ cells/ml with human MLR media described above. Lymphocytes from one donor were irradiated with 3000 rads from a cesium source and were designated "stimulator" cells. The second donor's lymphocytes were named "responder" cells. Five ml of each of the responder and stimulator cells were combined in a Corning T-25cm$^2$ tissue culture flask and incubated for seven days at 37° C., 5% $CO_2$ in air.

Part 2: Generation of target cells: Three days prior to harvest of the CTLs, lymphocytes were isolated from the donor whose lymphocytes were used as the stimulator cells in Part 1. These cells were adjusted to $1 \times 10^6$ cells/ml in human MLR media. Next, ten ml of cells and a 1:500 dilution of Difco PHA-P were combined in a Corning T-25 cm$^2$ tissue culture flask and incubated for 3 days at 37° C., 5% $CO_2$ in air.

Part 3: CTL Killing Assay (A 4-hour $^{51}$CR-release assay):

After 7 days of culture, CTLs (effector cells) were collected, washed three times, then adjusted to $1 \times 10^7$ cells/ml. Target cells were collected and washed two times. Target cells were labeled with 150 μCi Na$^{51}$CrO$_4$ (5 mCi/ml: Amersham Corp., Arlington Heights, Ill.) for approximately 1 hour at 37° C., 5% $CO_2$ in air. Cells were washed four times, counted, and adjusted to $2 \times 10^5$ cells/ml. The CTL killing assay was set up in a Corning 96-well round-bottom plate. A total of 200 μl cells was added per well. 50 μl of target cells and 100 μl of effector cells at various concentrations, and 50 μl of antibodies [H52, anti-CD11b, anti-CD11a, anti-CD18, and anti-gp120 (7F11), which are all publicly available] at 500 ng/ml were added in triplicate to the plate.

After four hours of incubation at 37° C., 5% $CO_2$ in air the supernatants were harvested (Skatron, Rockville, Md.) and their radioactivity was determined in an automatic gamma counter (Micromedic Systems, Horsham, Pa.). Percent specific cytotoxicity was calculated at 100×[cpm of test supernatants of effector cells and target cells incubated together (experimental release)]- [cpm of supernatants of target cells incubated alone (spontaneous release)]/{[cpm after lysis of target cells with 2% NP-40 (maximum release)]- [spontaneous release]}. Results determined were the mean of triplicate cultures ±/SD. Spontaneous release of target cells alone was <10% of maximum for all experiments.

II. Results:

A. Mixed Lymphocyte Response

Figure 8:
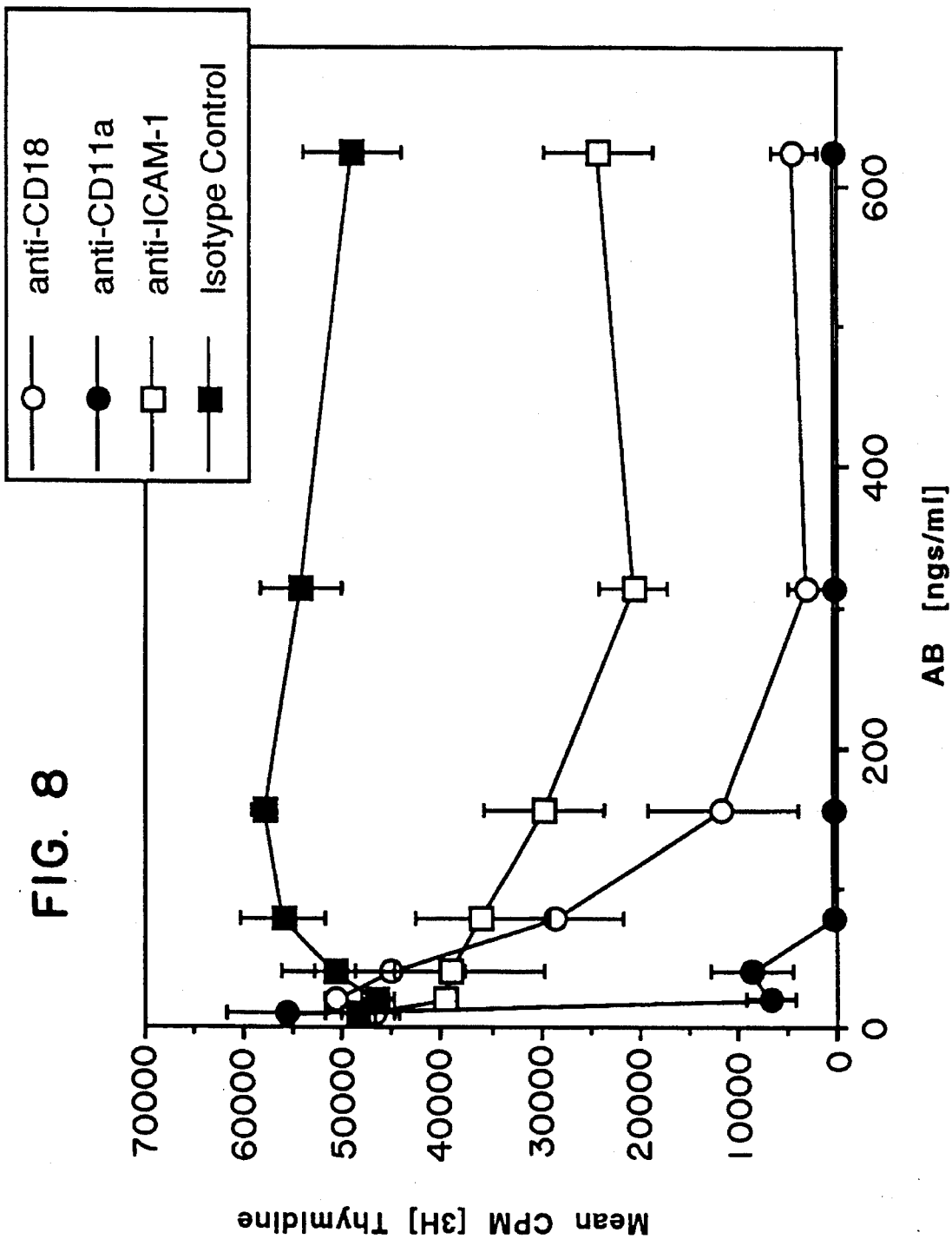
FIG. 8 shows the inhibitory effects of anti-CD18 (open circles), anti-CD11a (solid circles), anti-ICAM (open squares), and the isotype control (solid squares) on the human mixed lymphocyte response.

The results of the mixed lymphocyte response are shown in FIG. 8. It is clear that the anti-CD18 antibody has an inhibitory effect on the human mixed lymphocyte response, similar to that of the anti-CD11a response.

B. CTL Assay

Figure 9:
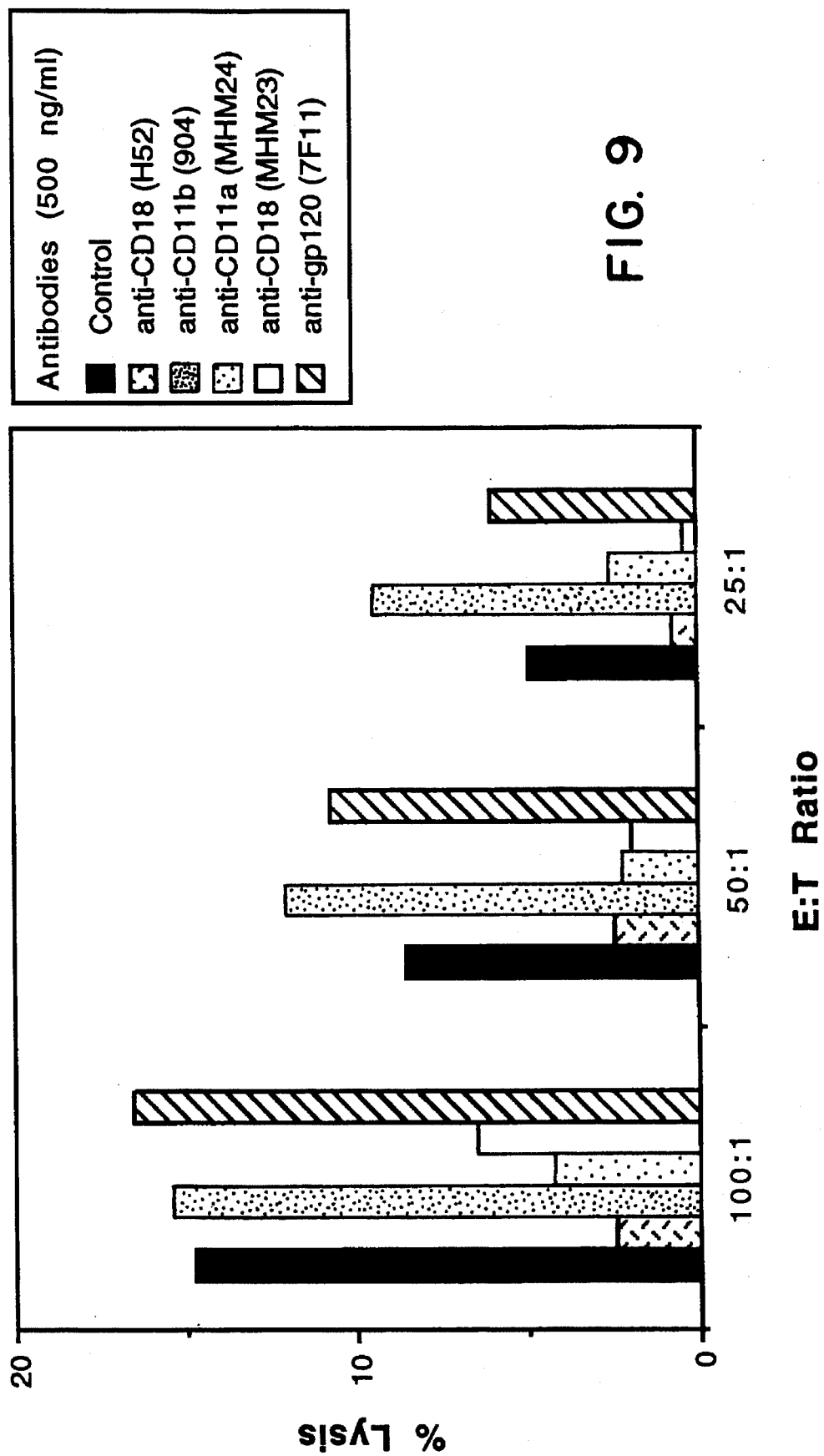
FIG. 9 shows the effect of control antibodies (solid bars), H52 (solid slashed bars), anti-CD11b (medium shaded bars), anti-CD11a (open slashed bars), anti-CD18 (open bars), and anti-gp120 (dark shaded bars) on cytotoxic T lymphocyte target cell killing.

The results of the effect of various antibodies on CTL target cell killing are shown in FIG. 9. They indicate that only H52, anti-CD11a, and anti-CD18 inhibit lysis of the cells.

It would be reasonably expected from the in vitro data above that the LFA-1 antagonist would function in an in vivo setting, i.e., in a transplantation.

EXAMPLE 4

Contact Sensitivity Model using anti-CD11a Antibody

Figure 10:
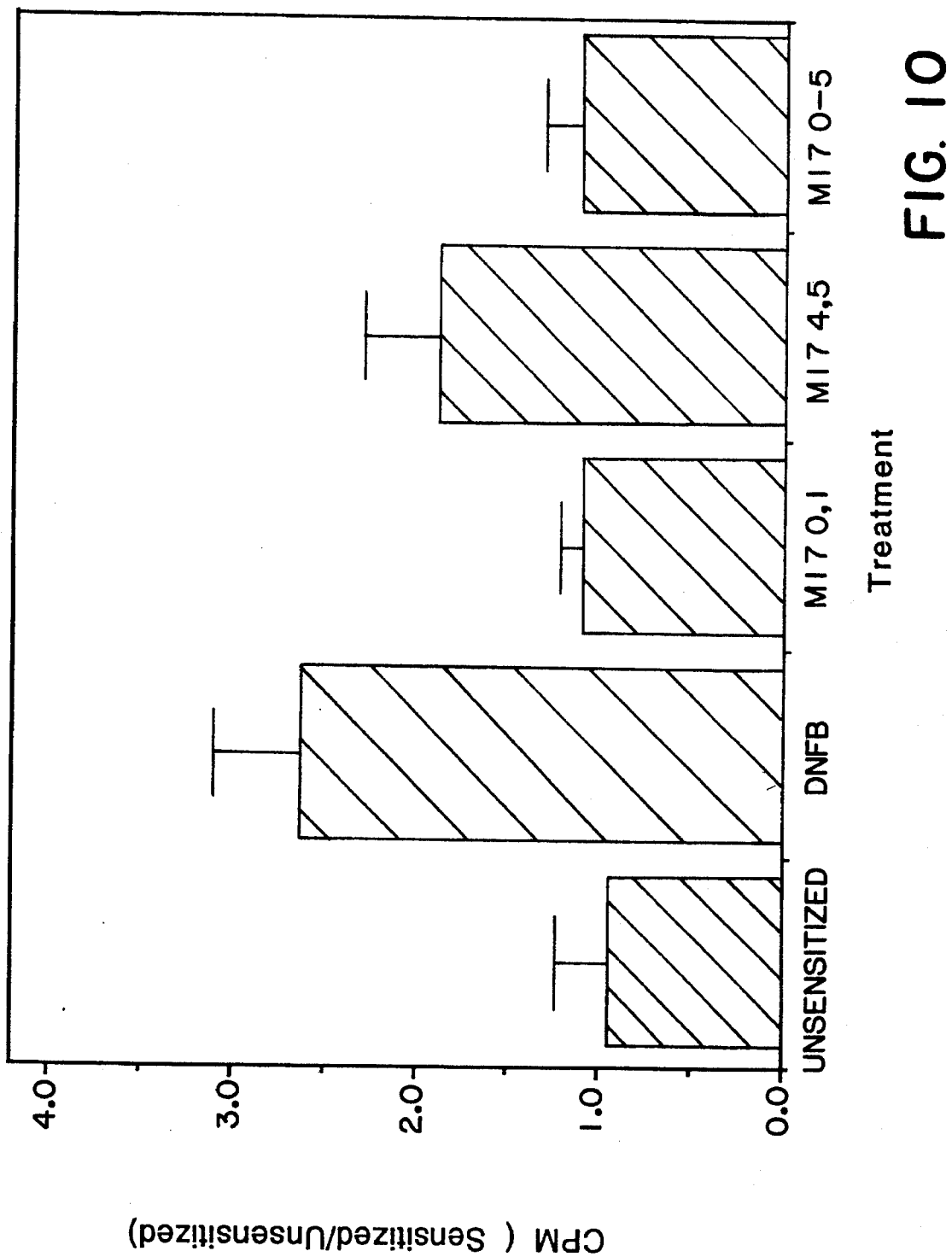
FIG. 10 shows the effect of M17 on contact sensitivity of mice to an immunogen, dinitrofluorobenzene.

The contact sensitivity model described below is a model for treating psoriasis.
Protocol:
Day 0: Sensitization BALB/c mice (4–6 weeks old) obtained from Charles River were divided into four treatment groups containing 6–8 mice per group. The mice were anesthetized i.p. with Ketamine/Xylazene/Acepromazine. A patch approximately 3×3 cm$^2$ was shaved on the abdomen of all the mice. A total of 50 µl of 10 mg/ml dinitrofluorobenzene (DNFB) was applied topically to the hair-free abdomen of the mice in groups 2–14. A PIPETMAN™ hand pipette was used to deliver the dose, enabling the wide end of the tip to be used to spread the DNFB over the skin.
Days 0–5: Administration of the Antibodies A total of 20 µg of the M17 antibody was injected i.p. on the days designated as follows: Group 1—days 0 and 1; Group 2—days 4 and 5; Group 3—days 0–5; and Group 4—rat IgG2a isotype control.
Days 0–5: Challenge The mice were anesthetized with Metaphane™ band anesthesia PIPETMAN™band pipette. With a hard pipette, 5 µl of DNFB was applied topically to each side of the left pinnae of the mice in groups 2–14 (5 µl/side). The wide end of the pipette tip was used to spread the DNFB over the ear. To each side of the right pinnae of the mice in groups 2–14 was applied topically 5 µl of the diluent of DNFB.
8 to 10 hours later after Challenge A total of 0.1 ml of 2 µCi $^{125}$I-UdR was injected i.v. into the tail vein of all mice.
16 to 18 Hours after $^{125}$I-UdR Injection The mice were sacrificed with $CO_2$. Both pinnae were cut off at the hairline of all mice. Left and right pinnae were put in separate tubes. Each pinnae was placed into appropriately labeled 12×75 polystyrene snap cap tubes. The pinnae were stored at −20° C.
Results The results are shown in FIG. 10. Those mice treated with M17 all exhibited a decreased sensitivity to DNFB as compared to the control. Those mice treated at days 0 and 1 and at days 0–5 exhibited the greatest decrease in sensitivity.

It would be expected that a decreased maintenance dose less than the 20 µg used in this experiment given intermittently after the initial dose would further decrease the sensitivity of the mice to the immunogen. Further, it would be reasonably expected that the in vivo mice data described above may be extrapolated to horses, cows, and other mammals, correcting for the body weight of the mammal in accordance with recognized veterinary and clinical procedures. Humans are believed to respond in this manner as well. Thus, it would be reasonably expected that in man the dosing regimen herein would have a beneficial restorative effect on immune function mediated by LFA-1 in all patients.

The treatment herein is expected to provide a higher therapeutic index than conventional and current therapy by minimizing toxicity to various parts of the body, including the kidneys (especially in the first few weeks after transplantation when the kidneys are most susceptible), the liver, the pancreas, the bones, the bone marrow, and the central nervous and immune systems. It is also expected to lessen the occurrence of both acute and chronic rejection. Further, the drug is expected to be useful in patients at high risk who are receiving regrafts and have a low one-year graft survival rate. Finally, the drug is expected to decrease morbidity in the patients, thus reducing the overall cost of transplantation.

What is claimed is:

1. A method for treating psoriasis in a mammal without depleting T-lymphocytes in the mammal comprising administering to the mammal an initial dosing of a therapeutically effective amount of an anti-LFA-1 antibody or an anti-ICAM-1 antibody, followed by a subsequent intermittent dosing of a therapeutically effective amount of the antibody that is less than 100%, calculated on a daily basis, of the initial dosing of the abtibody, wherein the antibody is administered to the mammal not more than once per week during the subsequent dosing.

2. The method of claim 1 wherein the subsequent dosing is less than about 50%, calculated on a daily basis, of the initial dosing of the antibody.

3. The method of claim 1 wherein the subsequent dosing is less than about 25%, calculated on a daily basis, of the initial dosing of the antibody.

4. The method of claim 1 wherein the subsequent dosing is less than about 10%, calculated on a daily basis, of the initial dosing of the antibody.

5. The method of claim 1 wherein the subsequent dosing is less than about 2%, calculated on a daily basis, of the initial dosing of the antibody.

6. The method of claim 1 further comprising administering an effective amount of an immunosuppressive agent to the mammal.

7. The method of claim 1 further comprising administering an effective amount of cyclosporin A to the mammal.

8. The method of claim 1 wherein the mammal is a human.

9. The method of claim I wherein the subsequent dosing is carried out for a longer time than the initial dosing.

10. The method of claim 6 wherein the initial dosing consists of daily administration.

11. The method of claim 1 wherein the subsequent dosing comprises administration of the antibody no more than once biweekly for at least about 5 weeks after the end of the initial dosing.

12. The method of claim 1 wherein the dosing is given by intravenous or subcutaneous injections.

13. The method of claim 1 wherein the antibody is an anti-LFA-1 antibody.

14. The method of claim 13 wherein the antibody is an anti-CD11a or anti-CD18 antibody.

15. The method of claim 13 wherein the antibody is an anti-CD11a antibody.

16. The method of claim 1 wherein the antibody is an anti-ICAM-1 antibody.

17. The method of claim 1 wherein the subsequent dosing is administered to the mammal for at least about 5 weeks after the initial dosing is terminated.

18. The method of claim 1 wherein the subsequent dosing is administered to the mammal for at least about 10 weeks after the initial dosing is terminated.

19. A method for prolonging survival of a transplanted graft in a mammalian host for greater than 200 days comprising administering to the mammalian host an initial dosing of a therapeutically effective amount of anti-LFA-1 antibody, followed by a subsequent intermittent dosing of a therapeutically effective amount of anti-LFA-1 antibody that is less than 100%, calculated on a daily basis, of the initial dosing of anti-LFA-1 antibody, wherein the subsequent intermittent dosing comprises administration of anti-LFA-1 antibody no more than once per week for at least about 10 weeks after the initial dosing is terminated, T lymphocytes are not depleted in the mammalian host, and the method results in specific immunosuppression.

20. The method of claim 19 wherein the anti-LFA-1 antibody is an anti-CD11a antibody or an anti-CD18 antibody.

21. The method of claim 20 wherein the anti-LFA-1 antibody is an anti-CD11a antibody.

22. The method of claim 19 wherein the subsequent dosing is less than about 50%, calculated on a daily basis, of the initial dosing of anti-LFA-1 antibody.

23. The method of claim 19 wherein the subsequent dosing is less than about 25%, calculated on a daily basis, of the initial dosing of anti-LFA-1 antibody.

24. The method of claim 19 wherein the subsequent dosing is less than about 10%, calculated on a daily basis, of the initial dosing of anti-LFA-1 antibody.

25. The method of claim 19 wherein the subsequent dosing is less than about 2%, calculated on a daily basis, of the initial dosing of anti-LFA-1 antibody.

26. The method of claim 19 wherein the initial dosing takes place before, during, and after transplantation has occurred.

27. The method of claim 19 further comprising administering an effective amount of an immunosuppressive agent to the mammal.

28. The method of claim 19 further comprising administering an effective amount of cyclosporin A to the mammal.

29. The method of claim 19 wherein the mammal is a human.

30. The method of claim 29 wherein the donor of the graft and the recipient are matched for HLA class II antigens.

31. The method of claim 19 wherein the subsequent dosing is carried out for a longer time than the initial dosing.

32. The method of claim 19 wherein the initial dosing consists of daily administration.

33. The method of claim 19 wherein the subsequent dosing comprises administration of anti-LFA-1 antibody no more than once biweekly.

34. The method of claim 19 wherein the initial dosing terminates from about 1 day to 4 weeks after transplantation has occurred and commences from about 1 week before transplantation occurs up to about simultaneously with the transplantation.

35. The method of claim 19 wherein the dosing is given by intravenous or subcutaneous injections.

36. A method for prolonging survival of a transplanted graft in a mammal without depleting T-lymphocytes in the mammal comprising administering to the mammal an initial dosing of a therapeutically effective amount of an anti-LFA-1 antibody or an anti-ICAM-1 antibody, followed by a subsequent intermittent dosing of a therapeutically effective amount of the antibody that is less than 100%, calculated on a daily basis, of the initial dosing of the antibody, wherein the antibody is administered to the mammal not more than once per week during the subsequent dosing.

37. The method of claim 36 wherein the antibody administered to the mammal is an anti-LFA-1 antibody.

* * * * *

UNITED STATES PATENT AND TRADEMARK OFFICE
CERTIFICATE OF CORRECTION

PATENT NO. : 5,622,700

DATED : April 22, 1997

INVENTOR(S) : Paula M. Jardieu, Bruce Montgomery

It is certified that error appears in the above-identified patent and that said Letters Patent is hereby corrected as shown below:

In claim 10, change [claim 6] to --claim 1--.

Signed and Sealed this

Twenty-sixth Day of August, 1997

Attest:

BRUCE LEHMAN

Attesting Officer

*Commissioner of Patents and Trademarks*